US008389008B2

(12) United States Patent
Baichwal et al.

(10) Patent No.: US 8,389,008 B2
(45) Date of Patent: *Mar. 5, 2013

(54) DELAYED RELEASE DOSAGE FORMS

(75) Inventors: Anand R. Baichwal, Wappingers Falls, NY (US); Paul Woodcock, Brookfield, CT (US); Raymond Higgins, New Milford, CT (US); Jaclyn Cobb, Niantic, CT (US)

(73) Assignee: Penwest Pharmaceuticals Co., Chadds Ford, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/943,356

(22) Filed: Sep. 17, 2004

(65) Prior Publication Data
US 2005/0112201 A1 May 26, 2005

Related U.S. Application Data

(60) Provisional application No. 60/504,035, filed on Sep. 19, 2003.

(51) Int. Cl.
*A61K 9/22* (2006.01)
(52) U.S. Cl. ......... 424/468; 424/464; 424/465; 424/474
(58) Field of Classification Search .................. 424/464, 424/468
See application file for complete search history.

(56) References Cited

U.S. PATENT DOCUMENTS

| 3,131,123 | A | 4/1964 | Masquelier | 167/57 |
|---|---|---|---|---|
| 4,248,858 | A | 2/1981 | Guley et al. | 424/21 |
| 4,432,966 | A | 2/1984 | Zeitoun et al. | 424/21 |
| 4,713,248 | A | 12/1987 | Kjornaes et al. | 424/468 |
| 4,780,318 | A | 10/1988 | Applegren et al. | 424/469 |
| 4,786,505 | A | 11/1988 | Lovgren et al. | 424/479 |
| 4,786,506 | A | 11/1988 | Fontanelli | 424/470 |
| 4,841,231 | A | 6/1989 | Angelucci | 324/73 |
| 4,842,867 | A | 6/1989 | Ayer et al. | 424/473 |
| 4,844,905 | A | 7/1989 | Ichikawa et al. | 424/451 |
| 4,851,231 | A | 7/1989 | Urquhart et al. | 424/469 |
| 4,853,230 | A | 8/1989 | Lovgren et al. | 424/466 |
| 4,853,249 | A | 8/1989 | Takashima et al. | 427/3 |
| 4,857,337 | A | 8/1989 | Miller et al. | 424/480 |
| 4,863,742 | A | 9/1989 | Panoz et al. | 424/473 |
| 4,871,549 | A | 10/1989 | Ueda et al. | 424/494 |
| 4,882,169 | A | 11/1989 | Ventouras | 424/493 |
| 4,886,669 | A | 12/1989 | Ventouras | 424/469 |
| 4,888,179 | A | 12/1989 | Applegren et al. | 424/480 |
| 4,894,240 | A | 1/1990 | Geoghegan et al. | 424/497 |
| 4,904,476 | A | 2/1990 | Mehta et al. | 424/456 |
| 4,910,021 | A | 3/1990 | Davis et al. | 424/456 |
| 4,933,186 | A | 6/1990 | Ohm et al. | 424/476 |
| 4,971,805 | A | 11/1990 | Kitanishi et al. | |
| 4,975,284 | A | 12/1990 | Stead et al. | 424/497 |
| 4,994,276 | A | 2/1991 | Baichwal et al. | 424/440 |
| 5,007,790 | A | 4/1991 | Shell | 424/451 |
| 5,032,406 | A | 7/1991 | Dansereau et al. | 424/472 |
| 5,035,899 | A | 7/1991 | Saeki et al. | 424/480 |
| 5,077,051 | A | * 12/1991 | Gallopo et al. | 424/435 |
| 5,096,717 | A | 3/1992 | Wirth et al. | 424/490 |
| 5,128,143 | A | 7/1992 | Baichwal et al. | 424/464 |
| 5,135,757 | A | 8/1992 | Baichwal et al. | 424/468 |
| 5,158,777 | A | 10/1992 | Abramowitz et al. | 424/458 |
| 5,169,639 | A | 12/1992 | Baichwal et al. | 424/468 |
| 5,175,003 | A | 12/1992 | Goldman | 424/484 |
| 5,190,765 | A | 3/1993 | Jao et al. | 424/473 |
| 5,202,338 | A | 4/1993 | Bar et al. | 514/314 |
| 5,217,720 | A | 6/1993 | Sekigawa et al. | 424/480 |
| 5,217,997 | A | 6/1993 | Levere et al. | 514/565 |
| 5,229,131 | A | 7/1993 | Amidon et al. | 424/451 |
| 5,232,706 | A | 8/1993 | Palomo Coll | 424/475 |
| 5,234,947 | A | 8/1993 | Cherksey | 514/449 |
| 5,238,686 | A | 8/1993 | Eichel et al. | 424/461 |
| 5,252,338 | A | 10/1993 | Jao et al. | 424/473 |
| 5,260,069 | A | 11/1993 | Chen | 424/451 |
| 5,262,172 | A | 11/1993 | Sipos | 424/490 |
| 5,275,824 | A | 1/1994 | Carli et al. | 424/490 |
| 5,294,448 | A | 3/1994 | Ring et al. | 424/497 |
| 5,296,233 | A | 3/1994 | Batista et al. | 424/463 |
| 5,302,400 | A | 4/1994 | Sipos | 424/494 |
| 5,310,558 | A | 5/1994 | Pozzi et al. | 424/476 |
| 5,316,772 | A | 5/1994 | Jurgens, Jr. et al. | 424/472 |
| 5,330,761 | A | 7/1994 | Baichwal | 424/469 |
| 5,334,372 | A | 8/1994 | Kawamata et al. | 424/78.03 |
| 5,374,759 | A | 12/1994 | Imperante et al. | 556/437 |
| 5,378,474 | A | 1/1995 | Morella et al. | 424/469 |
| 5,395,626 | A | 3/1995 | Kotwal et al. | 424/472 |
| 5,399,358 | A | 3/1995 | Baichwal et al. | 424/464 |

(Continued)

FOREIGN PATENT DOCUMENTS

DE 3943242 6/1990
EP 0305918 B1 3/1989

(Continued)

OTHER PUBLICATIONS

Maggi, L, Massolini, G., De Lorenzi, E., Caccialanza G., Conte, U.; "Stereoselective Release From Press-Coated Tablets"; Dept of Pharmaceutical Chemistry, University of Pavia, I-27100 Pavia, Italy.
Fukui, Eiji,; Uemura, Katsuji, ;Kobayashi, Masao; "Studies on Applicability of Press-Coated Tablets Using Hydroxypropylcellulose (HPC) in the Outer Shell for Timed Release Preparations", Journal of Controlled Release 68 (2000) 215-223.
Ross, Alistair C.; Chambers, Alan R.; Stevens, Howard N.E.; Johnson, James R., "A Novel Oral Probe Formulation: The Hydrophilic Sandwich (HS) Capsule", Dept. of Pharmaceutical Sciences, University of Strathclyde, Glasgow G4 ONR.
McConville, Jason T., Florence, Alastair J., Stevens, Howard N.E., Ross, Alistair C., "Processing Induced Variability of Time-Delayed Delivery From a Pulsatile Capsule Device", Dept. of Pharmaceutical Sciences, University of Strathclyde, Glasgow, G4 ONR.
Ross, Alistair C.; Stevens, Howard N.E.; MacRae, Ross J.; Walthier, Mathias, "The Influence of Tablet Erosion in Controlling Drug Rlease From a Time-Delayed Capsule Formulation", Dept. of Pharmaceutical Sciences, University of Strathclyde, Glasgow G4 ONR; Pfizer Central Research, Sandwich, CT 13 9NJ, Kent, U.K.

(Continued)

*Primary Examiner* — Jake M. Vu
(74) *Attorney, Agent, or Firm* — Davidson, Davidson & Kappel, LLC

(57) ABSTRACT

A delayed release pharmaceutical formulation comprising a core containing an active agent (e.g., a drug) and a delayed release compression coating comprising a natural or synthetic gum applied onto the surface of the core.

17 Claims, 2 Drawing Sheets

U.S. PATENT DOCUMENTS

| | | | |
|---|---|---|---|
| 5,399,359 A | 3/1995 | Baichwal | 424/464 |
| 5,399,362 A | 3/1995 | Baichwal et al. | 424/488 |
| 5,407,687 A | 4/1995 | Coffin et al. | 424/472 |
| 5,439,689 A | 8/1995 | Hendrickson et al. | 424/490 |
| 5,445,829 A | 8/1995 | Paradissis et al. | 424/480 |
| 5,455,046 A | 10/1995 | Baichwal | 424/457 |
| 5,464,633 A | 11/1995 | Conte et al. | 424/480 |
| 5,468,746 A | 11/1995 | Casagrande et al. | 514/235.5 |
| 5,472,708 A | 12/1995 | Chen | 424/451 |
| 5,472,711 A | 12/1995 | Baichwal | 424/468 |
| 5,478,574 A | 12/1995 | Baichwal et al. | 424/485 |
| 5,482,718 A | 1/1996 | Shah et al. | 424/480 |
| 5,500,227 A | 3/1996 | Oshlack et al. | 424/476 |
| 5,512,297 A | 4/1996 | Baichwal | 424/451 |
| 5,536,507 A | 7/1996 | Abramowitz et al. | 424/479 |
| 5,554,387 A | 9/1996 | Baichwal | 424/488 |
| 5,576,022 A | 11/1996 | Yang et al. | 424/472 |
| 5,585,114 A | 12/1996 | Besemer et al. | 424/488 |
| 5,612,053 A | 3/1997 | Baichwal et al. | 424/440 |
| 5,650,156 A | 7/1997 | Grinstaff et al. | 424/400 |
| 5,656,294 A * | 8/1997 | Friend et al. | 424/465 |
| 5,662,933 A | 9/1997 | Baichwal et al. | 424/457 |
| 5,667,801 A | 9/1997 | Baichwal | 424/457 |
| 5,670,168 A | 9/1997 | Baichwal et al. | 424/464 |
| 5,713,852 A | 2/1998 | Anthony et al. | 604/49 |
| 5,738,865 A | 4/1998 | Baichwal et al. | 424/440 |
| 5,773,025 A | 6/1998 | Baichwal | 424/458 |
| 5,788,987 A | 8/1998 | Busettii et al. | 424/480 |
| 5,792,476 A | 8/1998 | Hällgren | 424/465 |
| 5,811,388 A | 9/1998 | Friend et al. | 424/474 |
| 5,837,284 A | 11/1998 | Mehta et al. | 424/459 |
| 5,840,329 A | 11/1998 | Bai | 424/458 |
| 5,840,332 A * | 11/1998 | Lerner et al. | 424/464 |
| 5,846,563 A | 12/1998 | Baichwal | 424/457 |
| 5,858,412 A | 1/1999 | Staniforth et al. | 424/489 |
| 5,891,474 A | 4/1999 | Busetti et al. | 424/490 |
| 5,922,352 A | 7/1999 | Chen et al. | 424/465 |
| 5,958,456 A | 9/1999 | Baichwal et al. | 424/489 |
| 5,958,458 A | 9/1999 | Norling et al. | 424/490 |
| 5,958,873 A | 9/1999 | Sakr et al. | 514/2 |
| 6,024,982 A | 2/2000 | Oshlack et al. | 424/476 |
| 6,039,980 A | 3/2000 | Baichwal | 424/500 |
| 6,048,548 A | 4/2000 | Baichwal | 424/468 |
| 6,056,977 A | 5/2000 | Bhagwat et al. | 424/488 |
| 6,093,420 A * | 7/2000 | Baichwal | 424/468 |
| 6,103,263 A | 8/2000 | Lee et al. | 424/468 |
| 6,136,343 A | 10/2000 | Baichwal | 424/468 |
| 6,146,662 A | 11/2000 | Jao et al. | 424/473 |
| 6,156,340 A | 12/2000 | Adeyeye et al. | 424/463 |
| 6,190,692 B1 * | 2/2001 | Busetti et al. | 424/451 |
| 6,228,398 B1 * | 5/2001 | Devane et al. | 424/484 |
| 6,245,355 B1 | 6/2001 | Baichwal | 424/468 |
| 6,245,356 B1 | 6/2001 | Baichwal | 424/468 |
| 6,261,601 B1 | 7/2001 | Talwar et al. | 424/469 |
| 6,299,903 B1 | 10/2001 | Rivett et al. | 424/464 |
| 6,322,819 B1 | 11/2001 | Burnside et al. | 424/494 |
| 6,358,525 B1 | 3/2002 | Guo et al. | 424/464 |
| 6,365,185 B1 | 4/2002 | Ritschel et al. | 424/473 |
| 6,372,254 B1 | 4/2002 | Ting et al. | 424/473 |
| 6,387,394 B1 | 5/2002 | Baichwal et al. | 424/440 |
| 6,500,459 B1 * | 12/2002 | Chhabra et al. | 424/474 |
| 2003/0082230 A1 | 5/2003 | Baichwal et al. | 424/464 |
| 2003/0190360 A1 | 10/2003 | Baichwal et al. | 424/470 |

FOREIGN PATENT DOCUMENTS

| | | |
|---|---|---|
| EP | 0305918 A1 | 8/1989 |
| EP | 0366621 A1 | 2/1990 |
| EP | 0453001 A1 | 10/1991 |
| EP | 0519099 | 12/1992 |
| EP | 0572942 A2 | 12/1993 |
| EP | 0572942 B2 | 12/1993 |
| EP | 0629398 A1 | 12/1994 |
| EP | 0526862 | 2/1996 |
| EP | 0572942 B1 | 4/1997 |
| EP | 0 888 778 | 1/1999 |
| EP | 1064938 * | 1/2001 |
| EP | 1064938 A1 | 1/2001 |
| WO | 9116042 | 10/1991 |
| WO | WO96/40078 | 12/1996 |
| WO | 9826767 | 6/1998 |
| WO | 9832425 | 7/1998 |
| WO | 9832426 | 7/1998 |
| WO | 0054780 | 9/2000 |
| WO | 0143749 | 6/2001 |
| WO | 0174334 | 10/2001 |
| WO | WO 02/072033 * | 9/2002 |
| WO | WO02/072034 | 9/2002 |
| WO | WO03/066030 | 8/2003 |

OTHER PUBLICATIONS

Ross, Alistair C.; Stevens, Howard N.E; MacRae, Ross J.; Walter, Mathias, "Time-Delayed Capsule Drug Delivery Sysytem Based on Programmable Erosion", Dept. of Pharmaceutical Sciences, University of Strathclyde, Scotland. Pfizer Central Research, Sandwich, U.K.

Mitsuyuki, Matsuo; Nakamura, Chizuko; Arimori, Kazuhiko; Nakano, Masahiro, "Evaluation of Hydroxyethylcellulose as a Hydrophilic Swellable Material for Delayed Release Tablets", Dept. of Pharmaceutical Services, Kumamoto University Hospital, *Chem. Pharm. Bull.* 43(2) 311-314 (1995).

Conte, Ubaldo; Maggi, Lauretta, "A Flexible Technology for the Linear, Pulsatile and Delayed Release of Drugs, Allowing for Easy Accomodation of Difficult in Vitro Targets", Dept. of Pharmaceutical Chemistry, University of Pavia,*Joumal of Controlled Release* 64 (2000) 263-268.

Matsuo, Mitsuyuki; Arimori, Kazuhiko; Nakamura, Chizuko, Nakano, Masahiro,"Delayed-Release Tablets Using Hydroxyethylcellulose As a Gel-Forming Matrix", Dept. of Pharmaceutical Services, Kumanoto University Hospital, *International Journal of Pharmaceutics 138* (1996) 225-235.

Ross, Alistair, C.; Macrae, Ross J.; Walther, Mathias; Stevens, Howard N.E., "Chronopharmaceutical Drug Delivery From a Pulsatile Capsule Device Based on Programmable Erosion", Dept. of Pharmaceutical Sciences, University of Strathclyde, Glasgow and Pfizer Central Research, Sandwich, UK, *J. Pharm. Pharmacol.* (2000) 52: 903-909.

Sangalli, M.E..; Maroni, A.; Busetti, C.; Zema, L.; Giordano, F.; Gazzaniga, "In Vitro and In Vivo Evaluation of Oral Sysytems for Time and Site Specific Delivery of Drugs (Chronotopic® technology)", Instituto Chimico Farmaceutico, Universita di Milano,*Boll. Chim. Farmaceutico-Anno 138—n.3 Marzo 1999*, pp. 68-73.

Pillay, Viness; Fassihi, Reza, "In Situ Electrolyte Interactions in a Disk-Compressed Configuration System for Up-Curving and Constant Drug Delivery", Dept. of Pharmaceutical Sciences, School of Pharmacy, Temple University, *Jouranl of Controlled release 67* (2000) 55-65.

Kenyon, C.J.; Nardi, R.V.; Wong, D., Hooper, G.; Wilding, I.R.; Friend D.R., "Colonic Delivery of Dexamethasone: A Pharmacoscintigraphic Evaluation", *Aliment Pharmacol Ther 1997*: 11:205-213.

Abstract: El-Glbaly, Ibrahim, "Oral Delayed System based on Z-Pectinate Gel (ZPG) Microparticles As an Alternatecarrier to Calcium Pectinate Beads for Colonic Drug Delivery", *International Journal of Pharmaceutics (Kidlington)* vol. 232 No. 1-2, Jan. 31, 2002, pp. 199-211.

Nishimura, Kenji et al. "Dosage Form Design for Improvement of Bioavailablity of Levodopa VI: Formulation of Effervescent Enteric-Coated Tablets", Journal of American Pharmaceutical Sciences, vol. 73, No. 7, Jul. 1984, pp. 942-946.

Gazzaniga, A., et al. "Time-Dependent oral delivery systems for colon targeting", S.T.P. Pharma Sciences 5 (1), 1995, pp. 83-88.

International Search Report for PCT Application No. PCTUS04/30450.

Khan, M.Z.; "Recent Trends and Progress in Sustained or Controlled Oral Delivery of Some Water Soluble Drugs: Morphine Salts, Dilitiazem and Captopril" Drug Development and Industrial Pharmacy, 21(9), pp. 1037-1070 (1995).

Sinha V R et al: "Polysaccharides in colon-specific drug delivery", International Journal of Pharmaceutics, Elxevier BV, NL, vol. 224, No. 1-2, (2001).

Supplementary European Search Report issued on Aug. 17, 2011.

* cited by examiner

DELAYED RELEASE DOSAGE FORMS

This application claims priority from U.S. Provisional Application No. 60/504,035, filed Sep. 19, 2004, the disclosure of which is hereby incorporated by reference in its entirety.

FIELD OF THE INVENTION

The present invention relates to a dosage form for oral administration that preferentially deliver drugs to the colon. The present invention is further related to methods of preparing such formulations, and to methods of treatment utilizing such formulations.

BACKGROUND OF THE INVENTION

Specific delivery of drugs and pharmaceutical compositions to the colon is important in the treatment of a wide variety of diseases and conditions. Colon diseases include such conditions such as Crohn's disease, colitis (particularly ulcerative colitis), irritable bowel syndrome and the like. These diseases include a spectrum of inflammatory bowel disorders with overlapping clinical, epidemiologic and pathologic findings but without a definite etiology. Both Crohn's disease and ulcerative colitis are characterized by chronic inflammation at various sites of the GI tract, generally the colon (i.e., that part of the intestine from the cecum to the rectum). Crohn's disease seems to affect the cecum primarily while ulcerative colitis seems to go past the second turn in the colon and affect the splenic flexure.

Targeting of drugs to the colon provides the ability to locally treat large bowel diseases, thus avoiding or decreasing systemic effects of drugs or inconvenient and painful trans-colonic administration of drugs. Furthermore, there is an increased need for delivery to the colon of drugs that are reported to be absorbable in the colon, such as steroids, which would increase the efficiency of the treatment and enable the reduction in the required effective dose. Godbillon, J., et al., Br. J. Clin. Pharmacol. 19:113S (1985); Antonin, K. H. et al., Br. J. Clin. Pharmacal. 19:137S (1985); Fara, J. W., 3rd International Conference on Drug Absorption, Edinburgh (1988); for a review see Rubinstein, A., Biopharm. Drug Dispos. 11:465-475 (1990).

There have been previous attempts to provide oral controlled release delivery systems capable of passing over the entire tract of the small intestine, including the duodenum, jejunum, and ileum, so that the active ingredients can be released directly in the colon, if such site specific delivery is desired. However, the targeting of drugs to desired locations in the alimentary canal can be complicated. Because of its location at the distal portion of the alimentary canal, the colon is particularly difficult to access. The design of orally administered colonic delivery systems must take into account factors such as the pH of the alimentary canal and the presence of enzymes in the stomach and small intestine. The high acidity of the gastric tract and presence of proteolytic and other enzymes therein generates a highly digestive environment that readily disintegrates pharmaceutical formulations that do not possess some type of gastro-resistance protection. This disintegration would typically have a detrimental effect upon the delayed release of the active agent.

PCT publications WO 02/072033 and WO 02/072034, the disclosures of which are hereby incorporated by reference, disclose chronotherapeutic pharmaceutical formulations comprising a core containing an active agent (e.g., a drug) and a delayed release compression coating comprising a natural or synthetic gum applied onto the surface of the core.

It is considered desirable by those skilled in the art to provide an oral controlled release delivery system that is adaptable to delay the release of a drug(s) such that the drug is delivered to the colon of a human.

OBJECTS AND SUMMARY OF THE INVENTION

It is an object of the present invention to provide an oral pharmaceutical dosage form that releases a drug(s) into the colon of a human after oral ingestion of the dosage form.

It is a further object of certain embodiments of the present invention to provide an oral pharmaceutical dosage form that provides a delayed release of a drug(s) into the gastrointestinal tract of a human such that said drug is released in the colon.

It is a further object of certain embodiments of the present invention to provide an oral pharmaceutical dosage form having a core containing drug, the core being compression coated with a coating that provides a delayed release of the drug from the dosage form after the dosage form is orally administered to a human.

It is a further object of certain embodiments of the present invention to provide an oral pharmaceutical dosage form having a drug-containing core that is compression coated with a coating which provides a delayed release of the drug when the dosage form is orally administered to a human.

It is a further object of certain embodiments of the present invention to provide a dosage form which allows colon-specific dosing for a wide variety of diseases.

It is a further object of certain embodiments of the present invention to provide a dosage form which allows colon-specific dosing for diseases such as ulcerative colitis, Crohn's disease or other diseases which are typically more symptomatic in lower gastrointestinal tract.

It is a further object of certain embodiments of the present invention to provide a dosage form which provides a delayed release of drug from the dosage form such that the drug is release in the colon, followed by a sustained release of the drug thereafter.

It is a further object of certain embodiments of the present invention to provide a compression coated dosage form having an immediate release layer of a drug(s) overcoating a compression coated core which provides a delayed release of the same or different drug(s) from the dosage form; the core optionally providing a sustained release of the drug thereafter.

It is a further object of certain embodiments of the present invention to provide an oral dosage form which provides site-specific delivery of drug (e.g., to the colon).

It is a further object of certain embodiments of the present invention to develop an oral dosage form which provides programmed release of drug.

It is a further object of certain embodiments of the present invention to develop an oral dosage form which provides pulsatile release of drug.

In accordance with the above-mentioned objects of the invention, the present invention is directed in part to an oral solid dosage form, which comprises A delayed release oral solid dosage form comprising: a core comprising a therapeutically effective amount of a drug which can be absorbed in the colon and an optional pharmaceutically acceptable excipient (e.g., a diluent); and a delayed release material compression coated onto the surface of said core, said delayed release material comprising one or more natural or synthetic gums; said dosage form providing substantially no release of drug until at least 6 hours, or at least about 8 hours after the start of an in-vitro dissolution test using USP apparatus type III with 250 mL solution (pH 1.5) at 15 dpm (dips per minute).

In certain embodiments, the present invention is further directed to a delayed release oral solid dosage form, comprising a core comprising a therapeutically effective amount of a drug, and a compression coating material compression coated onto said core, the compression coating material comprising one or more natural or synthetic gums, said compression coating delaying the release of said drug from said dosage form such that after oral administration to humans the initial release of said drug from the dosage form does not occur at least until after entry into the mid small bowel.

In certain embodiments, the present invention is further directed to a delayed release oral solid dosage form, comprising a core comprising a therapeutically effective amount of a drug, and a delayed release material compression coated onto said core, said delayed release material comprising one or more natural or synthetic gums, the compression coating delaying the release of said drug from said dosage form such that after oral administration to humans the initial release of said dosage form does not occur until after entry into the mid small bowel and complete release does not occur until the dosage form reaches the colon.

In certain embodiments, the present invention is further directed to a delayed release oral solid dosage form, comprising a core comprising a therapeutically effective amount of a drug, and a delayed release material compression coated onto said core, said delayed release material comprising one or more natural or synthetic gums, said compression coating providing an in-vitro dissolution rate of the dosage form, when measured by the USP apparatus type III with 250 ml solution pH 1.5 at 15 dpm that is 0% drug released at about 3 hours, from about 5% to about 40% (by wt) drug released after 4 hours, from about 30% to about 90% (by wt) drug released after 5 hours and greater than about 60% (by wt) drug released after 6 hours, such that after oral administration to humans the initial release of said drug from the dosage form does not occur at least until after entry into the mid small bowel after administration to humans.

In certain embodiments, the present invention is further directed to a delayed release oral solid dosage form, comprising a core comprising a therapeutically effective amount of a drug, and a delayed release material compression coated onto said core, the delayed release material comprising one or more natural or synthetic gums, the compression coating delaying the release of said drug from said dosage form such that after oral administration to humans the dosage form releases at least 50 percent of the drug in the colon.

In certain embodiments, the present invention is further directed to a delayed release oral solid dosage form, comprising a core comprising a therapeutically effective amount of a drug, from about 5 to about 20% disintegrant, and a delayed release material compression coated onto said core, the delayed release material comprising one or more natural or synthetic gums, the compression coating delaying the release of said drug from said dosage form until after the drug has reached at least the nid small bowel after oral administration to humans.

In certain preferred embodiments, the disintegrant is a superdisintegrant incorporated in the core in an amount effective to cause the release of at least about 50 percent of the drug(s) into the colon within one hour upon completion of the time period for delayed release.

In certain preferred embodiments, the compression coating comprises a mixture (e.g., matrix) of xanthan gum, locust bean gum, and a pharmaceutically acceptable saccharide, e.g., a monosaccharide, a disaccharide, a polyhydric alcohol, or a combination of any of the foregoing. In certain preferred embodiments, the core is an immediate release core comprising the drug together with one or more pharmaceutically acceptable excipients.

In certain embodiments, the invention is further directed in part to a delayed release oral solid dosage form comprising a core comprising a therapeutically effective amount of a drug (s), and an agglomerated delayed release material compression coated onto the core, the agglomerated delayed release material comprising a gum selected from, e.g., a homopolysaccharide, a heteropolysaccharide, and a mixture of a homopolysaccharide and a heteropolysaccharide, together with a pharmaceutically acceptable excipient, the compression coating such that after oral administration to humans, the drug is released in the colon.

The invention is further directed in part to a delayed release oral solid dosage form comprising a core comprising a therapeutically effective amount of a drug(s) and a disintegrant, and a delayed release material compression coated onto the core, said delayed release material comprising one or more natural or synthetic gums, said compression coating delaying the release of the drug from the dosage form for a predetermined period of time (e.g., until the dosage form reaches the colon of a human after oral administration), the disintegrant being included in the core in an amount such that at least about 50 percent of the drug is released into said colon within one hour after said drug enters the colon.

The invention is further directed in part to a delayed release oral solid tablet, comprising a tablet core comprising a therapeutically effective amount of a drug, and a delayed release material compression coated onto the core, the delayed release material comprising one or more natural or synthetic gums, the gums comprising from about 6.5 percent to about 83 percent of the tablet by weight, the compression coating delaying the release of the drug from the dosage form such that after oral administration to a human at least 50% of said drug is released in the colon.

The invention is further directed to a delayed release oral solid dosage form for low dose drugs, comprising a core comprising from about 0.01 mg to about 40 mg of a drug(s), and a delayed release material compression coated onto the core, the delayed release material comprising one or more natural or synthetic gums, the compression coating comprising from about 75 to about 94 percent by weight of the oral solid dosage form, and the ratio of the core to gum in the compression coating being from about 1:0.37 to about 1:5, by weight, the compression coating delaying the release of the drug from the dosage form such that after oral administration to a human at least 50% of said drug is released in the colon.

The invention is further directed in part to a delayed release oral solid dosage form for a relatively high dose drug, comprising a core comprising from about 41 mg to about 300 mg of a drug, and a delayed release material compression coated onto the core, the delayed release material comprising one or more natural or synthetic gums, the ratio of the core to gum in the compression coating being from about 1:0.3 to about 1:3, by weight, the oral solid dosage form having a total weight from about 500 mg to about 1500 mg.

The invention is further directed in part to a method of preparing a delayed release oral solid dosage form of a drug, comprising preparing a core comprising a therapeutically effective amount of a drug(s) and from about 5 to about 20% disintegrant, by weight of the core, preparing a granulate of a delayed release material comprising one or more natural or synthetic gums, compression coating the granulate onto the core, the compression coating delaying the release of the drug from the dosage form until after the drug has reached at least the mid small bowel after oral administration to humans. In certain preferred embodiments, the method further comprises preparing the granulate of delayed release material by wet granulating one or more natural or synthetic gums together with at least one pharmaceutically acceptable excipient, and drying the resultant granulate to obtain agglomerated particles of the delayed release material. In certain embodiments the method further comprises granulating the glucocorticosteroid, the disintegrant, and a pharmaceutically acceptable inert diluent prior to the compression coating step.

In certain preferred embodiments, the disintegrant is a superdisintegrant incorporated in the core in an amount effective to cause the release of at least about 50 percent of the drug(s) into the colon within one hour upon completion of the time period for delayed release.

The invention is further directed to methods of treatment utilizing the formulations disclosed herein. In certain preferred embodiments, the invention of the present invention is directed to a method of treating Crohn's disease and/or ulcerative colitis using the formulations disclosed herein.

In certain embodiments, the oral dosage form provides a lag time (delayed release of drug) such that said drug is released in at least the mid small bowel of a human, after oral administration to a human.

In certain embodiments, the initial release of the drug from the dosage form does not occur until after entry of the dosage form into the distal small bowel. In certain alternate embodiments, the initial release of the drug from the dosage form does not occur until after entry of the dosage form into the ileocaecal junction. In certain embodiments, the initial release of the drug from the dosage form does not occur until after entry of the dosage form into the ascending colon. In certain embodiments, the initial release of the drug from the dosage form does not occur until after entry of the dosage form into the hepatic flexure. In certain embodiments, the initial release of the drug from the dosage form does not occur until after entry of the dosage form into the transverse colon.

In certain embodiments, the delayed release oral solid dosage form of the present invention provides an in-vitro dissolution rate, when measured by the USP apparatus type III with 250 ml solution pH 1.5 at 15 dpm that is 0% drug released after 3 hours, from about 10% to about 40% (by wt.) drug released after 4 hours, from about 60% to about 90% (by wt.) drug released after 5 hours, and greater than about 85% (by wt.) drug released after 6 hours.

In certain embodiments, the delayed release oral solid dosage form of the present invention provides an in-vitro dissolution rate, when measured by the USP apparatus type III with 250 ml solution pH 1.5 at 15 dpm, where no substantial amount of drug is released at 6 hours.

In certain embodiments, the delayed release oral solid dosage form of the present invention provides an in-vitro dissolution rate, when measured by the USP apparatus type III with 250 ml solution pH 1.5 at 15 dpm, where no substantial amount of drug is released at 4 hours.

In certain embodiments, the delayed release oral solid dosage form of the present invention provides a mean Tmax at from about 2 to about 10 hours after oral administration. Preferably the delayed release oral solid dosage form provides a mean Tmax at from about 2 to about 8 hours after oral administration.

In certain embodiments, at least 75 percent of said drug is released from the dosage form in the colon. In certain embodiments, at least 90 percent of said drug is release from the dosage form in the colon.

In certain embodiments, the delayed release oral solid dosage form provides an initial release of drug at about 4.91±1.44 hours after oral administration to humans and complete release at about 6.05±3.31 after administration to humans.

In certain embodiments, the delayed release oral solid dosage form provides an initial release of drug at about 3.34±0.89 hours after oral administration to humans and complete release occurs at about 3.71±0.94 after administration to humans.

In certain embodiments, the delayed release oral solid dosage form provides an initial release of drug at about 3.10±0.69 hours after oral administration to humans and complete release occurs at about 3.28±0.71 after administration to humans.

In certain embodiments, the delayed release oral solid dosage form provides a local therapeutic effect.

In certain embodiments, the delayed release oral solid dosage form provides a systemic therapeutic effect.

In certain embodiments, the delayed release oral solid dosage form of provides a local and systemic therapeutic effect.

In certain preferred embodiments, the oral dosage form releases at least about 50 percent of the drug(s) contained in the core within about one hour, and preferably at least about 80 percent of the drug(s) contained in the core within about one or two hours, after the end of the lag time provided by the compression coating.

In certain embodiments, the oral dosage form of the invention provides a lag time such that after oral administration of the oral dosage form to a mammal the drug is released in at least the mid small bowel after oral administration to humans.

In certain preferred embodiments, the oral dosage form provides a lag time of about 2 to about 6 hours after oral administration of the dosage form.

In certain preferred embodiments, the oral dosage form provides a lag time of about 6 to about 7 hours with full release by about 8 to about 9 hours, after oral administration of the dosage form.

In certain other preferred embodiments, the oral dosage form provides a lag time of about 6 to about 7 hours, followed by full release of the drug by about 7 to about 8 hours after oral administration.

In yet other embodiments, the formulation provides a lag time from about 9 to about 12 hours, with full release by about 11 to about 13 hours after oral administration, preferably a lag time of about 10 to about 11 hours followed by full release at about 11 to about 12 hours after oral administration of the dosage form.

In yet other embodiments, the formulation provides a lag time of, e.g., about 3-12 hours, with full release of the drug from the dosage form within about 24 hours, or (alternatively) after 24 hours.

By "delayed release" it is meant for purposes of the present invention that the release of the drug is delayed and the drug contained in the dosage form is not substantially released from the formulation until after a certain period of time, e.g., such that the drug is not released into the bloodstream of the human immediately upon ingestion by the human of the tablet but rather only after a specific period of time, e.g., when the dosage form is in the colon. For purposes of the present invention, delayed release includes "timed delay" or a release of drug after a lag time, or a programmed release.

By "the drug is released in at least the mid small bowel" it is meant for purposes of the present invention that the drug is not released prior to entry of the mid small bowel (e.g., the drug is not release in the stomach or the proximal small bowel), but is released in the mid small bowel or after the mid small bowel (e.g., the drug may be released in the ascending colon, the transverse colon, etc.).

By "sustained release" it is meant for purposes of the present invention that, once the drug is released from the formulation, it is released at a controlled rate such that therapeutically beneficial blood levels (but below toxic levels) of the medicament are maintained over an extended period of time from the start of drug release, e.g., providing a release over a time period, e.g., from about 4 to about 24 hours from the point of drug release after the lag time, onward.

The term "Cmax" is meant for purposes of the present invention to mean the maximum plasma concentration of a medicament achieved after single dose administration of a dosage form in accordance with the present invention.

The term "Tmax" is meant for purposes of the present invention to mean the elapsed time from administration of a dosage form to the time the Cmax of the medicament is achieved.

The term "mean" for purposes of the present invention, when used to define a pharmacokinetic value (e.g., Tmax) represents the arithmetic mean value measured across a patient population.

The term "environmental fluid" is meant for purposes of the present invention to encompass, e.g., an aqueous solution (e.g., an in-vitro dissolution bath) or gastrointestinal fluid.

The term "substantially no release", means less than about 5% released, preferably less than about 2% released, preferably less than about 1% released, preferably less than about 0.5% released, or most preferably 0% released.

The term "initial release", means at least about 5% released, preferably at least about 2% released, preferably at least about 1% released, preferably at least about 0.5% released or most preferably >0% released.

The term "complete release", means at least about 95% released, preferably at least about 98% released, preferably at least about 99% released, preferably at least about 99.5% released or most preferably 100% released.

The term USP apparatus type III used herein is described e.g., in the United States Pharmacopeia XXV (2002).

DETAILED DESCRIPTION OF THE INVENTION

Figure 1:
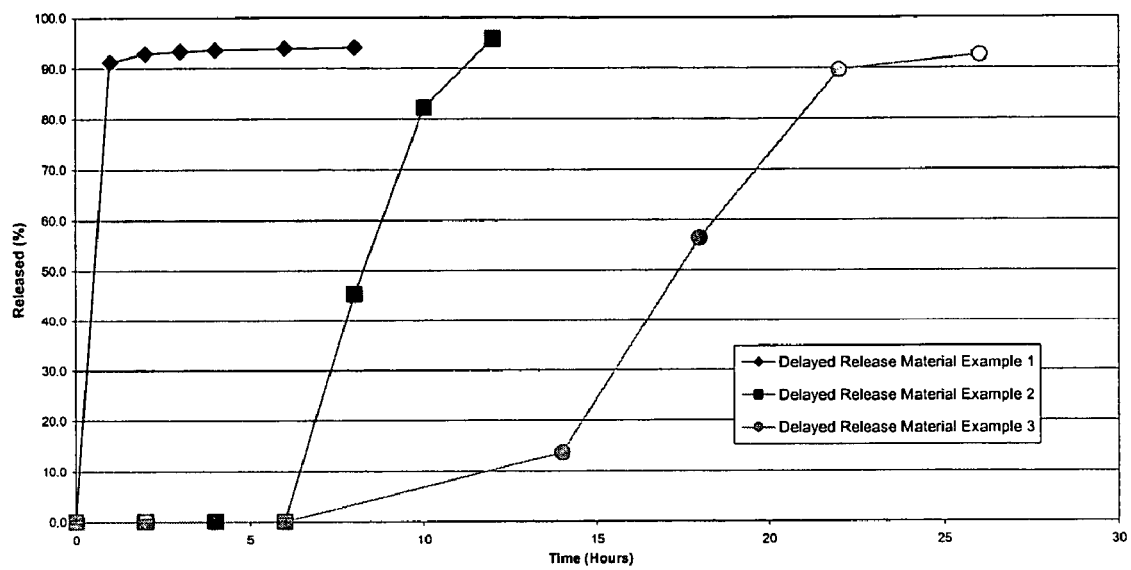
FIG. 1. is a graph which depicts the average release profile of the formulations of Examples 15, 16, and 17, which are compression-coated with the delayed release material of Examples 1, 2, and 3, respectively, as tested by the USP apparatus type III dissolution method, changing the pH from 1.5 to 5.5 to 7.5
Figure 2:
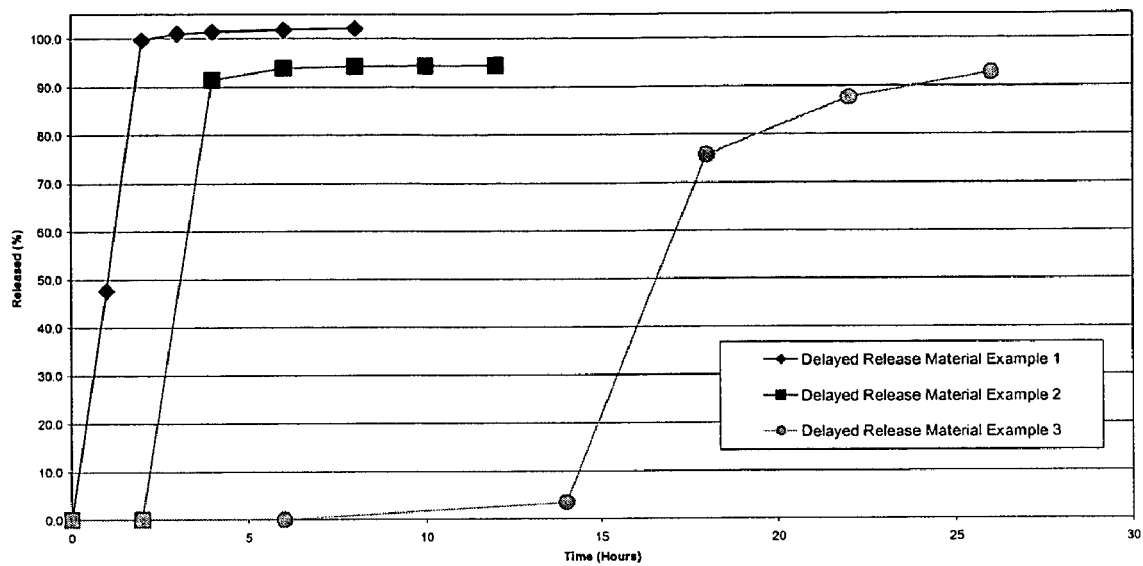
FIG. 2. is a graph which depicts the average release profile of the formulations of Examples 15, 16, and 17, which are compression-coated with the delayed release material of Examples 1, 2, and 3, respectively, as tested by the USP apparatus type III dissolution method at a pH of 1.5.

The present invention may be employed to achieve the delayed release of a pharmaceutically active agent and in certain embodiments to provide a controlled-release pharmaceutical formulation for pharmaceutically active agents that are desirously delivered over a predetermined period of time. The formulations of the present invention provide the delayed release of a pharmaceutically active agent and may be useful for the treatment of conditions that are desirously treated through delayed pharmaceutical agent delivery mechanisms. For example, the formulations of the present invention are useful for the treatment of colon diseases, i.e., conditions, diseases or other illnesses, such as Crohn's disease and ulcerative colitis, the symptoms of which are generally more likely to affect the colon. These conditions may be treated by administering the delayed release formulation according to the present invention to the patient such that the delivery of the pharmaceutically active agent is preferably in the colon, or preferably the pharmaceutically active agent has been delivered from the dosage form (and absorbed from the colon) to an extent that it has achieved a therapeutic effect, thereby alleviating the symptoms of the disease.

The formulations of the present invention comprise a core comprising an active agent and a compression coating over the core that comprises one or more natural or synthetic pharmaceutically acceptable gums. In certain especially preferred embodiments, the compression coating comprises a combination of a heteropolysaccharide gum (e.g., xanthan gum) and a homopolysaccharide gum (e.g., locust bean gum), together with a pharmaceutically acceptable saccharide (e.g., lactose, dextrose, mannitol, etc.). In certain preferred embodiments, the gum(s) are wet granulated together with the optional saccharide(s) to form agglomerated particles comprising a mixture of, e.g., xanthan gum, locust bean gum and dextrose.

The goal of the compression coating of the present invention is to delay the release of the active agent, for a predetermined period of time, referred to in the art as a "lag time." In certain embodiments, the release of the active agent is delayed for, or has a lag time of, about 2 to about 18 hours after administration of the dosage form. Preferably the lag time is such that the drug is released from the dosage form in the colon of the mammal (e.g., human) after oral administration.

The core comprising the active agent can be formulated for either immediate release or sustained release of the active agent. Formulations for both immediate release and sustained release of active agents are well known to those skilled in the art.

In the present invention, when the core comprising the active agent is formulated for immediate release, the core can be prepared by any suitable tableting technique known to those skilled in the art. For example, the pharmaceutically active agent may be admixed with excipient(s) and formed into a tablet core using a conventional tableting press or using conventional wet granulation techniques. According to certain preferred embodiments of the present invention, ingredients for the core are dry blended in a V-blender and compressed on a rotary tablet press into tablet cores. Alternatively, in certain embodiments, the ingredients for the core can be wet granulated, dried and thereafter compressed into tablet cores. Preferably, the core should be compressed to a degree of hardness such that they do not chip or come apart during further processing, such as during the coating process. In certain embodiments, the cores can be compressed to 50 mg weight and 2 to 8, preferably 4 to 8, most preferably 4-5 kP hardness. In addition, tablet core size should range from ⅛ inch to ⅝ inch, preferably from ⅛ inch to ½ inch, more preferably from 3/16 inch to ¼ inch.

In certain embodiments, wherein the core is manufactured without a wet granulation step, and the final mixture is to be compressed into a tablet core, all or part of the excipient in the core may comprise a pre-manufactured direct compression diluent. Examples of such pre-manufactured direct compression diluents include Emcocel® (microcrystalline cellulose, N.F.) and Emdex® (dextrates, N.F.), which are commercially available from JRS Pharma LP., Patterson, N.Y.) and TabFine® (a number of direct-compression sugars including sucrose, fructose and dextrose). Other direct compression diluents include anhydrous lactose (Lactose N.F., anhydrous direct tableting) from Sheffield Chemical, Union, N.J. 07083; Elcems® G-250 (powdered cellulose), N.F.) from Degussa, D-600 Frankfurt (Main) Germany; Fast-Flo Lactose® (Lactose, N.F., spray dried) from Foremost Whey Products, Baraboo, Wis. 53913; Maltrin® (Agglomerated maltodextrin) from Grain Processing Corp., Muscatine, Iowa 52761; Neosorb 60® (Sorbitol, N.F., direct-compression from Roquet Corp., 645 5th Ave., New York, N.Y. 10022; Nu-Tab® (Compressible sugar, N.F.) from Ingredient Technology, Inc., Pennsauken, N.J. 08110; Polyplasdone XL® (Crospovidone, N.F., cross-linked polyvinylpyrrolidone) from GAF Corp., New York, N.Y. 10020; Primojel® (Sodium starch glycolate, N.F., carboxymethyl starch) from Generichem Corp., Little Falls, N.J. 07424; Solka Floc® (Cellulose floc); Spray-dried lactose® (Lactose N.F., spray dried) from Foremost Whey Products, Baraboo, Wis. 53913 and DMV Corp., Vehgel, Holland; and Sta-Rx 1500® (Starch 1500) (Pregelatinized starch, N.F., compressible) from Colorcon, Inc., West Point, Pa. 19486. In certain embodiments of the present invention, the directly compressible inert diluent which is used in the core of the present invention is an augmented microcrystalline cellulose as disclosed in U.S. Pat. No. 5,585,115, issued Dec. 17, 1996, and entitled "PHARMACEUTICAL EXCIPIENT HAVING IMPROVED COMPRESSIBILITY", hereby incorporated by reference in its entirety. The augmented microcrystalline cellulose described therein is commercially available under the tradename Prosolv® from JRS Pharma.

Alternatively, in certain embodiments, the core comprising the active agent can be formulated as a sustained release core for the sustained release of the active agent. When the core comprising the active agent is formulated for sustained release, the core can be prepared in a number of ways known in the art. For example, the active agent can be incorporated in a sustained release matrix and thereafter compressed into a core, or a sustained release material can be coated onto the immediate release core to provide for the sustained release of the active agent, or a combination of the compressed sustained release matrix and sustained release coating on the core can be used. Additionally, spheroids comprising the active agent, or multiparticulates with sustained release coatings and comprising the active agent, may be compressed with optional binders and other excipients into a sustained release core.

When the core of the present invention comprises a sustained release matrix, the matrix formulations are generally prepared using standard techniques well known in the art. Typically, they are prepared by dry blending a sustained release material, diluent, active agent, and optional other excipients followed by granulating the mixture until proper granulation is obtained. The granulation is done by methods known in the art. Typically with a wet granulation, the wet granules are dried in a fluid bed dryer, sifted and ground to appropriate size. Lubricating agents are mixed with the dried granulation to obtain the final core formulation.

In our U.S. Pat. Nos. 4,994,276; 5,128,143; 5,135,757; 5,455,046; 5,512,297; 5,554,387; 5,667,801; 5,846,563; 5,773,025; 6,048,548; 5,662,933; 5,958,456; 5,472,711; 5,670,168; and 6,039,980, all of which are hereby incorporated by reference, we reported that a controlled release excipient that is comprised of a gelling agent such as synergistic heterodisperse polysaccharides (e.g., a heteropolysaccharide such as xanthan gum) preferably in combination with a polysaccharide gum capable of cross-linking with the heteropolysaccharide (e.g., locust bean gum) is capable of processing into oral solid dosage forms using either direct compression, following addition of drug and lubricant powder, conventional wet granulation, or a combination of the two. These systems (controlled release excipients) are commercially available under the trade name TIMERx® from Penwest Pharmaceuticals Co, Patterson, N.Y., which is the assignee of the present invention.

In certain embodiments of the present invention, wherein the core provides for the sustained release of the active agent, the core comprises a sustained release matrix such as those disclosed in our foregoing patents. For example, in certain embodiments of the present invention, in addition to the active agent, the core comprises a sustained release excipient comprising a gelling agent comprising a heteropolysaccharide gum and a homopolysaccharide gum capable of cross-linking said heteropolysaccharide gum when exposed to an environmental fluid, and an inert pharmaceutical diluent. Preferably, the ratio of the heteropolysaccharide gum to the homopolysaccharide gum is from about 1:3 to about 3:1, and the ratio of active agent to gelling agent is preferably from about 1:3 to about 1:8. The resulting core preferably provides a therapeutically effective blood level of the active agent for at least about 4 hours, and in certain preferred embodiments, for about 24 hours. In certain preferred embodiments, the sustained release excipient further comprises an effective amount of a pharmaceutically acceptable ionizable gel strength enhancing agent, such as those described hereinafter, to provide a sustained release of the active when the core is exposed to an environmental fluid. The sustained release excipient (with or without the optional ionizable gel strength enhancing agent) may be further modified by incorporation of a hydrophobic material which slows the hydration of the gums without disrupting the hydrophilic matrix. In addition, in certain embodiments, the sustained release excipient can be modified to provide for bi- or multi-phasic release profiles of the active agent by the inclusion of a pharmaceutically acceptable surfactant or wetting agent in the core. Alternatively, the sustained release excipient comprises only one of the aforementioned gums. In yet other embodiments, the sustained release excipient comprises a different pharmaceutically acceptable gum.

In addition to the above, other sustained release materials may be used for the sustained release matrix cores of the inventive formulations. A non-limiting list of suitable sustained-release materials which may be included in a sustained-release matrix according to the present invention include hydrophilic and/or hydrophobic materials, such as sustained release polymers, gums, acrylic resins, protein derived materials, waxes, shellac, and oils such as hydrogenated castor oil, hydrogenated vegetable oil. Preferred sustained-release polymers include alkylcelluloses such as ethylcellulose, acrylic and methacrylic acid polymers and copolymers; and cellulose ethers, especially hydroxyalkylcelluloses (especially hydroxypropylmethylcellulose) and carboxyalkylcelluloses. Preferred waxes include for example natural and synthetic waxes, fatty acids, fatty alcohols, and mixtures of the same (e.g., beeswax, carnauba wax, stearic acid and stearyl alcohol). Certain embodiments utilize mixtures of any of the foregoing sustained release materials in the matrix of the core. However, any pharmaceutically acceptable hydrophobic or hydrophilic sustained-release material which is capable of imparting sustained-release of the active agent may be used in accordance with the present invention.

Alternatively, in certain embodiments of the present invention, the core may be formulated to provide for the sustained release of the active agent through the use of an immediate release core (as previously described) with a sufficient amount of a hydrophobic coating to provide for the sustained release of the active agent from the immediate release core.

The hydrophobic coating may be applied to the core using methods and techniques known to those skilled in the art. Examples of suitable coating devices include fluid bed coaters, pan coaters, etc. Examples of hydrophobic materials which may be used in such hydrophobic coatings include for example, alkylcelluloses (e.g., ethylcellulose), copolymers of acrylic and methacrylic acid esters, waxes, shellac, zein, hydrogenated vegetable oil, mixtures thereof, and the like.

Additionally, the cores may be formulated for sustained release of the active agent by using a combination of the sustained release matrix and sustained release coating. The sustained release cores (e.g, sustained release matrix, sustained release coated, or combination thereof), and the immediate release cores, may also contain suitable quantities of additional excipients, e.g., lubricants, binders, granulating aids, diluents, colorants, flavorants and glidants which are conventional in the pharmaceutical art.

Specific examples of pharmaceutically acceptable diluents and excipients that may be used in formulating the cores are described in the *Handbook of Pharmaceutical Excipients*, American Pharmaceutical Association (1986), incorporated by reference herein.

In certain embodiments the cores of the present invention, particularly the immediate release cores, include a surfactant, which contributes to the release of the active agent from the dosage form. In certain embodiments, the surfactant is in an effective amount to facilitate the release of the drug from the dosage form upon exposure of the dosage form to an aqueous solution. In certain preferred embodiments, the surfactant is included in an amount that facilitates the immediate release of the drug from the core of the dosage form upon exposure of the dosage form to an aqueous solution. For example, in certain embodiments, after the dosage form is exposed to an aqueous solution, the coating of the dosage form delays the release of the drug from the dosage form by delaying the exposure of the core to the aqueous solution, after the aqueous solution is exposed to the core, the inclusion of the surfactant in the core promotes the release of the drug from the core (e.g., by promoting dissolution of the drug the into the aqueous solution).

In certain preferred embodiments, the inclusion of the surfactant in the core of the dosage form facilitates the complete release of the drug from the dosage form in less than 4 hours after initial release, preferably in less than 3 hours after initial release, more preferably in less 2 hours after initial release, and most preferably in less than 1 hour after initial release.

Surfactants for use in the present invention include pharmaceutically acceptable anionic surfactants, cationic surfactants, amphoteric (amphipathic/amphophilic) surfactants, and non-ionic surfactants. Suitable pharmaceutically acceptable anionic surfactants include, for example, monovalent alkyl carboxylates, acyl lactylates, alkyl ether carboxylates, N-acyl sarcosinates, polyvalent alkyl carbonates, N-acyl glutamates, fatty acid-polypeptide condensates, sulfuric acid esters, alkyl sulfates (including sodium lauryl sulfate (SLS)), ethoxylated alkyl sulfates, ester linked sulfonates (including docusate sodium or dioctyl sodium succinate (DSS)), alpha olefin sulfonates, and phosphated ethoxylated alcohols.

Suitable pharmaceutically acceptable cationic surfactants include, for example, monoalkyl quaternary ammonium salts, dialkyl quaternary ammonium compounds, amidoamines, and aminimides.

Suitable pharmaceutically acceptable amphoteric (amphipathic/amphophilic) surfactants, include, for example, N-substituted alkyl amides, N-alkyl betaines, sulfobetaines, and N-alkyl β-aminoproprionates.

Other suitable surfactants for use in conjunction with the present invention include polyethyleneglycols, esters or ethers thereof. Examples include polyethoxylated castor oil, polyethoxylated hydrogenated castor oil, polyethoxylated fatty acid from castor oil or polyethoxylated fatty acid from hydrogenated castor oil. Commercially available surfactants that can be used are known under trade names Cremophor, Myrj, Polyoxyl 40 stearate, Emerest 2675, Lipal 395 and PEG 3350.

In certain preferred embodiments, certain combinations of the aforementioned surfactants are used in the cores of the dosage forms of the present invention. In certain preferred embodiment, the surfactant includes the combination of two or more surfactants (e.g., PEG and sodium lauryl sulfate). In certain embodiments in which the therapeutic active drug is formulated for immediate release, when no surfactant is present, a controlled profile may be produced.

In certain embodiments, the one or more surfactants included in the core is in an amount of from about 5 to about 50 percent, preferably from about 10 to about 30 percent, by weight of the core. In terms of whole tablet weight (e.g., core plus compression coating), the one or more surfactant(s) in the core are included in an amount of from about 1 to about 20 percent, preferably from about 2 to about 10 percent, by weight of the tablet (entire formulation).

In certain preferred embodiments, the oral dosage form includes one or more disintegrants preferably incorporated in the core. When such an agent is included in the core, the rate of release of drug (after the initial delay caused by the compression coating) is an immediate pulse effect. In certain embodiments, when no disintegrant is present, a controlled profile may be produced. Suitable disintegrants are known to those skilled in the art, and include for example sodium starch glycolate (commercially available as Explotab® from JRS Pharma LP).

The mechanism of disintegration is based on swelling, wicking, and deformation of the disintegrants. When a compressed tablet is placed in aqueous solution, water can be quickly absorbed, and the swelling of the disintegrant breaks apart tablets quickly. In one embodiment in which the therapeutic active drug is formulated for immediate release, when a disintegrant is present in the core of the tablet, the rate of release of the active agent is an immediate pulse effect. In certain embodiments in which the therapeutic active drug is formulated for immediate release, when no disintegrant is present, a controlled profile may be produced.

Examples of such disintegrants for use in the present invention include, for example, starch, veegum, crospovidone, cellulose, kaolin, microcrystalline cellulose (e.g., Avicel PH101 & PH102), crosslinked polyvinyl pyrrolidone (e.g., Kollidon CL), and mixtures thereof. In certain preferred embodiments, the disintegrant is a superdisintegrant, such as, for example, croscarmellose sodium, crospovidone, crosslinked carboxy methyl cellulose, sodium starch glycolate, and mixtures thereof. Superdisintegrants can be incorporated at lower levels than regular disintegrants to increase the water content. Some brand named superdisintegrants for use in the present invention include, Ac-Di-Sol®, Primojel®, Explotab®, and Crospovidone®.

In certain embodiments, the core of the present invention includes a wicking agent in addition to or as an alternative to a disintegrant. Wicking agents such as those materials already mentioned as disintegrants (e.g. microcrystalline cellulose) may be included if necessary to enhance the speed of water uptake. Other materials suitable for acting as wicking agents include, but are not limited to, colloidal silicon dioxide, kaolin, titanium dioxide, fumed silicon dioxide, alumina, niacinamide, sodium lauryl sulfate, low molecular weight polyvinyl pyrrolidone, m-pyrol, bentonite, magnesium aluminum silicate, polyester, polyethylene, mixtures thereof, and the like.

In certain embodiments, the one or more disintegrant(s) in the core is included in an amount from about 5 to about 20 percent, preferably from about 6 to about 10 percent, most preferably about 8 percent by weight of the core. In terms of whole tablet weight (e.g., core plus compression coating), the one or more disintegrant(s) in the core are included in an amount from about 0.1 to about 5 percent, preferably from about 0.3 to about 2 percent, by weight of the tablet (entire formulation).

According to the present invention, the core containing active drug is completely surrounded or substantially surrounded by a compression coating. The compression coating preferably delays the release of the pharmaceutically active agent for a predetermined period of time, which time is dependent upon the formulation of the coating and the thickness of the coating layer. In certain embodiments, the appropriate time period for the release of the active ingredient can be determined prior to the preparation of the formulation, and the formulation can be designed by applying the appropriate thickness and composition of the coating to achieve the desired time delay prior to release of the active ingredient and the desired release rate of the active ingredient following the time delay.

Preferably, the compression coating comprises a natural or synthetic gum which can function as a gelling agent, causing the core to be surrounded by the gel when the compression coated tablet is exposed to an environmental fluid (e.g., water or gastrointestinal fluid) and thereby causing the drug to be released after diffusion of the environmental fluid through the compression coating, the dissolution of the drug into the environmental fluid, and the egress of the dissolved drug into the fluid surrounding the compression coated tablet.

In certain embodiments, gums for use in the compression coating include, for example and without limitation, heteropolysaccharides such as xanthan gum(s), homopolysaccharides such as locust bean gum, galactans, mannans, vegetable gums such as alginates, gum karaya, pectin, agar, tragacanth, accacia, carrageenan, tragacanth, chitosan, agar, alginic acid, other polysaccharide gums (e.g. hydrocolloids), and mixtures of any of the foregoing. Further examples of specific gums which may be useful in the compression coatings of the invention include but are not limited to acacia catechu, salai guggal, indian bodellum, copaiba gum, asafetida, cambi gum, Enterolobium cyclocarpum, mastic gum, benzoin gum, sandarac, gambier gum, butea frondosa (Flame of Forest Gum), myrrh, konjak mannan, guar gum, welan gum, gellan gum, tara gum, locust bean gum, carageenan gum, glucomannan, galactan gum, sodium alginate, tragacanth, chitosan, xanthan gum, deacetylated xanthan gum, pectin, sodium polypectate, gluten, karaya gum, tamarind gum, ghatti gum, Accaroid/Yacca/Red gum, dammar gum, juniper gum, ester gum, ipil-ipil seed gum, gum talha (acacia seyal), and cultured plant cell gums including those of the plants of the genera: acacia, actinidia, aptenia, carbobrotus, chickorium, cucumis, glycine, hibiscus, hordeum, letuca, lycopersicon, malus, medicago, mesembryanthemum, oryza, panicum, phalaris, phleum, poliathus, polycarbophil, sida, solanum, trifolium, trigonella, Afzelia africana seed gum, Treculia africana gum, detarium gum, cassia gum, carob gum, Prosopis africana gum, Colocassia esulenta gum, Hakea gibbosa gum, khaya gum, scleroglucan, zea, mixtures of any of the foregoing, and the like.

In certain especially preferred embodiments, the compression coating comprises a heteropolysaccharide such as xanthan gum, a homopolysaccharide such as locust bean gum, or a mixture of one or more hetero- and one or more homopolysaccharide(s). Heterodisperse excipients, previously disclosed as a sustained release tablet matrix in our U.S. Pat. Nos. 4,994,276, 5,128,143, and 5,135,757, may be utilized in the compression coatings of the present invention. For example, in certain embodiments of the present invention, a gelling agent of both hetero- and homo-polysaccharides which exhibit synergism, e.g., the combination of two or more polysaccharide gums producing a higher viscosity and faster hydration than that which would be expected by either of the gums alone, the resultant gel being faster-forming and more rigid, may be used in the compression coatings of the present invention.

The term "heteropolysaccharide" as used in the present invention is defined as a water-soluble polysaccharide containing two or more kinds of sugar units, the heteropolysaccharide having a branched or helical configuration, and having excellent water-wicking properties and immense thickening properties.

An especially preferred heteropolysaccharide is xanthan gum, which is a high molecular weight ($>10^6$) heteropolysaccharide. Other preferred heteropolysaccharides include derivatives of xanthan gum, such as deacylated xanthan gum, the carboxymethyl ether, and the propylene glycol ester.

The homopolysaccharide materials used in the present invention that are capable of cross-linking with the heteropolysaccharide include the galactomannans, i.e., polysaccharides that are composed solely of mannose and galactose. A possible mechanism for the interaction between the galactomannan and the heteropolysaccharide involves the interaction between the helical regions of the heteropolysaccharide and the unsubstituted mannose regions of the galactomannan. Galactomannans that have higher proportions of unsubstituted mannose regions have been found to achieve more interaction with the heteropolysaccharide. Hence, locust bean gum, which has a higher ratio of mannose to galactose, is especially preferred as compared to other galactomannans, such as guar and hydroxypropyl guar.

In certain preferred embodiments, the heteropolysaccharide comprises from about 1 to about 50 percent and the homopolysaccharide material comprises from about 50 to about 1 percent by weight of the compression coating. In certain preferred embodiments, the ratio of heteropolysaccharide to homopolysaccharide material is from about 1:3 to 3:1, preferably from about 2:3 to 3:2, or 1:1.

In a certain preferred embodiment, the compression coating comprises from about 5 to about 70 percent or more by weight of a hydrophilic material (e.g., gums). In certain preferred embodiments of the present invention, the higher the percentage of gums in the compression coating, the longer the delay of the release or "lag time" of the active agent.

In certain embodiments, the percent of gums in the compression coating corresponds to a delayed release of the active agent which is independent of pH. For example, in certain preferred embodiments, when the compression coating is less than about 25% gums, preferably comprising about 5 to about 15% gums, the delayed release is more independent of pH than a compression coating comprising greater than about 25% gums (e.g., 30, 40, or 50% gums).

In certain preferred embodiments, the compression coating also includes pharmaceutically acceptable excipients, for example, a saccharide such as a monosaccharide, a disaccharide or a polyhydric alcohol, and/or mixtures of any of the foregoing, or microcrystalline cellulose or a starch. Examples of suitable such excipients include sucrose, dextrose, lactose, fructose, xylitol, sorbitol, mannitol, starches, mixtures thereof and the like. In certain embodiments, it is preferred that a soluble pharmaceutical excipient such as lactose, dextrose, sucrose, mannitol, or mixtures thereof is included in the materials to be used in the compression coating. In certain preferred embodiments, the gum(s) is wet granulated with the pharmaceutically acceptable excipient prior to its use as a compression coating on the surface of the inner cores of the invention. The compression coating may comprise, e.g., up to about 95% pharmaceutically acceptable excipient(s), by weight.

In certain embodiments, the amount of gum(s) contained in the compression coating is from about 1 percent to about 90 percent by weight, preferably from about 6.5 percent to about 83 percent of the total tablet, by weight.

In certain embodiments, it is possible to dry mix the ingredients of the compression (delayed release) coating without utilizing a wet granulation step. If the mixture is to be manufactured without a wet granulation step, and the final mixture is to be compression coated onto a pre-formed tablet core, it is preferred that all or part of the pharmaceutically acceptable excipient(s) should impart sufficient compressibility to provide a pharmaceutically acceptable product. The properties and characteristics of a specific excipient system prepared according to the present invention may be dependent in part on the individual characteristics, e.g., of the homo- and heteropolysaccharide constituents, in terms of polymer solubility, glass transition temperatures etc., as well as on the synergism both between different homo- and heteropolysaccharides and between the homo- and heteropolysaccharides and the inert saccharide constituent(s) in modifying dissolution fluid-excipient interactions.

In certain embodiments of the invention where the compression coating comprises a heteropolysaccharide, a homopolysaccharide, or both, a release-modifying agent as described in our previous patents directed to the use of these materials in sustained release matrices can also be utilized in the compression coating. Such release-modifying agents and pre-manufactured excipients disclosed in our U.S. Pat. Nos. 5,455,046; 5,512,297; 5,554,387; 5,667,801; 5,846,563; 5,773,025; 6,048,548; 5,662,933; 5,958,456; 5,472,711; 5,670,168; and 6,039,980 may be utilized in the compression coatings of the present invention.

Thus, for example, the release-modifying agent may comprise an ionizable gel-strength enhancing agent. The ionizable gel strength-enhancing agent that is optionally used in conjunction with the present invention may be monovalent or multivalent metal cations. The preferred salts are the inorganic salts, including various alkali metal and/or alkaline earth metal sulfates, chlorides, borates, bromides, citrates, acetates, lactates, etc. Specific examples of suitable ionizable gel strength enhancing agent include calcium sulfate, sodium chloride, potassium sulfate, sodium carbonate, lithium chloride, tripotassium phosphate, sodium borate, potassium bromide, potassium fluoride, sodium bicarbonate, calcium chloride, magnesium chloride, sodium citrate, sodium acetate, calcium lactate, magnesium sulfate and sodium fluoride. Multivalent metal cations may also be utilized. However, the preferred ionizable gel strength-enhancing agents are bivalent. Particularly preferred salts are calcium sulfate and sodium chloride. The ionizable gel strength enhancing agents of the present invention are added in an amount effective to obtain a desirable increased gel strength due to the cross-linking of the gelling agent (e.g., the heteropolysaccharide and homopolysaccharide gums). In alternate embodiments, the ionizable gel strength-enhancing agent is included in the delayed release excipient of the present invention in an amount from about 1 to about 20% by weight of the delayed release excipient, and in an amount 0.5% to about 16% by weight of the final dosage form. In certain embodiments, the inclusion of an ionizable gel strength-enhancing agent not only delays the release of the active, but also provides for a sustained release of the active agent.

In certain embodiments of the present invention, the (delayed release) compression coating coated onto the core comprises from about 1 to about 90 percent by weight of a gelling agent comprising a heteropolysaccharide gum and a homopolysaccharide gum, from about 0 to about 20 percent by weight of an ionizable gel strength enhancing agent, and from about 10 to about 95 percent by weight of an pharmaceutically acceptable excipient. In other embodiments, the compression coating material comprises from about 5 to about 75 percent gelling agent (gum), from about 0 to about 15 percent ionizable gel strength enhancing agent, and from about 30 to about 95 percent pharmaceutically acceptable excipient (e.g., an inert diluent). In yet other embodiments, the compression coating material comprises from about 7.5 to about 50 percent gelling agent, from about 0 to about 10 percent ionizable gel strength enhancing agent, and from about 30 to about 95 percent pharmaceutically acceptable excipient.

Surfactants that may be used in the present invention generally include pharmaceutically acceptable anionic surfactants, cationic surfactants, amphoteric (amphipathic/amphophilic) surfactants, and non-ionic surfactants. Suitable pharmaceutically acceptable anionic surfactants include, for example, monovalent alkyl carboxylates, acyl lactylates, alkyl ether carboxylates, N-acyl sarcosinates, polyvalent alkyl carbonates, N-acyl glutamates, fatty acid-polypeptide condensates, sulfuric acid esters, alkyl sulfates (including sodium lauryl sulfate (SLS)), ethoxylated alkyl sulfates, ester linked sulfonates (including docusate sodium or dioctyl sodium succinate (DSS)), alpha olefin sulfonates, and phosphated ethoxylated alcohols.

Suitable pharmaceutically acceptable cationic surfactants include, for example, monoalkyl quaternary ammonium salts, dialkyl quaternary ammonium compounds, amidoamines, and aminimides.

Suitable pharmaceutically acceptable amphoteric (amphipathic/amphophilic) surfactants, include, for example, N-substituted alkyl amides, N-alkyl betaines, sulfobetaines, and N-alkyl β-aminoproprionates.

Other suitable surfactants for use in conjunction with the present invention include polyethyleneglycols as esters or ethers. Examples include polyethoxylated castor oil, polyethoxylated hydrogenated castor oil, or polyethoxylated fatty acid from castor oil or polyethoxylated fatty acid from hydrogenated castor oil. Commercially available surfactants that can be used are known under trade names Cremophor, Myrj, Polyoxyl 40 stearate, Emerest 2675, Lipal 395 and PEG 3350.

Other release-modifying pharmaceutically acceptable agents that may be added in appropriate quantities for their particular ability to modify dissolution rates include, for example: stearic acid, metallic stearates, stearyl alcohol, hydrogenated cotton seed oil, sodium chloride and certain disintegrants that are described below.

The quantity of such release-modifying agent employed depends on the release characteristics required and the nature of the agent. For a delayed release formulation according to the invention, the level of release-modifying agents used may be from about 0.1 to about 25%, preferably from about 0.5 to about 10% by weight of the total composition.

In certain other embodiments of the invention, the compression coating includes a pH-modifying agent. The pH-modifying agent may be present in the compression coating from about 1% to about 10% by weight of the final dosage form. In preferred embodiments, the pH-modifying agent is an organic acid such as citric acid, succinic acid, fumaric acid, malic acid, maleic acid, glutaric acid or lactic acid.

In certain preferred embodiments, the release of drug occurs when aqueous environmental fluid (e.g., water or gastrointestinal fluid, etc. surrounding the dosage form) diffuses through the compression coating of the dosage form, resulting in hydration of the core and dissolving the drug, which then can pass into the fluid surrounding the core.

In certain preferred embodiments, the delayed release of the drug (lag time) is varied by increasing the thickness of the compression coating (increased lag time) or by decreasing the thickness of the compressing coating (decreased lag time). The delayed release may also be varied, e.g., by changing the gum(s) included in the delayed release compression coating, selecting a particular combination of gums, by including or not including a pharmaceutically acceptable excipient, such as a saccharide (including polysaccharides) or a combination of saccharide(s) (or polysaccharides) in the compression coating, by changing or by adding additional agents to the compression coating which cause the compression coating to further delay the diffusion of water (or gastrointestinal fluid) through the compression coating (e.g., matrix) into the inner core (thereby allowing hydration of the inner core). In addition, the compression force used to apply the compression coating may be used to alter the release rate of the active ingredient. Also, release can be modified via the use of an extragranular excipient addition to the compression coating. Such ingredients may comprise, for example, microcrystalline cellulose, polyvinylpyrrolidone, polyethylene glycol, and the like.

The delayed release of the drug may further be varied by utilizing a further coating (i) between the core and the compression coating; (ii) over the compression coating; or (iii) both between the core and the compression coating and over the compression coating. Such coatings may comprise, for example a hydrophilic polymer (such as hydroxypropylmethylcellulose) and/or a hydrophobic polymer (such as an acrylic polymer, a copolymer of acrylic and methacrylic acid esters, an alkylcellulose such as ethylcellulose, etc.). In such circumstances, the release of drug from the dosage form may not only be occurring as fluid diffuses through the compression coating; erosion of the further coatings described in this paragraph may also delay the release of drug.

The dissolution rates of the present invention (with or without the optional release modifying agents mentioned above) may be further modified by incorporation of a hydrophobic material in the compression coating, which slows the hydration of the gums without disrupting the hydrophilic matrix. This is accomplished in alternate embodiments of the present invention by granulating the delayed release excipient with a solution or dispersion of a hydrophobic material prior to the compression coating of the core. The hydrophobic polymer may be selected from an alkylcellulose such as ethylcellulose, other hydrophobic cellulosic materials, polymers or copolymers derived from acrylic or methacrylic acid esters, copolymers of acrylic and methacrylic acid esters, zein, waxes, shellac, hydrogenated vegetable oils, and any other pharmaceutically acceptable hydrophobic material known to those skilled in the art. The solvent for the hydrophobic material may be an aqueous or organic solvent, or mixtures thereof. The amount of hydrophobic material incorporated into the delayed release excipient is that which is effective to slow the hydration of the gums without disrupting the hydrophilic matrix formed upon exposure to an environmental fluid. In certain preferred embodiments of the present invention, the hydrophobic material is included in the compression coating in an amount from about 1 to about 20 percent by weight.

The compression coating may also contain suitable quantities of, e.g., lubricants, binders, granulating aids, diluents, colorants, flavorants and glidants which are described hereinafter and are which are conventional in the pharmaceutical art.

In preferred embodiments where the materials to be included in the compression coating are pre-manufactured, the combination of the gum gelling agent (e.g., a mixture of xanthan gum and locust bean gum) with the pharmaceutical excipient(s), with or without a release modifying agent, provides a ready-to-use compression coating product in which a formulator need only apply the material onto the core by compression coating to provide the desired delayed release dosage forms. The compression coating may comprise a physical admix of the gums along with a soluble excipient such as compressible sucrose, lactose, dextrose, etc., although it is preferred to granulate or agglomerate the gums with a plain pharmaceutically acceptable excipient (i.e., crystalline) sucrose, lactose, dextrose, mannitol, etc., to form a delayed release excipient for use in the compression coating. The granulate form has certain advantages including the fact that it can be optimized for flow and compressibility.

The gums and optional pharmaceutical excipients used in the compression coating are preferably prepared according to any agglomeration technique to yield an acceptable excipient product. In wet granulation techniques, the desired amounts of the hydrophilic material (e.g., heteropolysaccharide gum and/or the homopolysaccharide gum) and the inert diluent are mixed together and thereafter a moistening agent such as water, propylene glycol, glycerol, alcohol or the like is added to prepare a moistened mass. Next, the moistened mass is dried. The dried mass is then milled with conventional equipment into granules. Thereafter, the excipient product is ready to use.

The (preferably) pre-manufactured delayed release excipient is preferably free-flowing and directly compressible. Accordingly, the excipient may be directly compressed onto a pre-formed inner core of a therapeutically active medicament to form coated tablets. The delayed release coating mixture, in an amount sufficient to make a uniform coating onto a pre-formed tablet core, is subjected to tableting in a conventional production scale tableting machine at normal compression pressure, i.e., about 2000-1600 lbs/sq in. However, the mixture should not be compressed to such a degree that there is subsequent difficulty in its hydration when exposed to gastric fluid.

The average particle size of the granulated delayed release excipient of the present invention ranges from about 50 microns to about 400 microns and preferably from about 185 microns to about 265 microns. The particle size of the granulation is not narrowly critical, the important parameter being that the average particle size of the granules must permit the formation of a directly compressible excipient which forms a coating over pharmaceutically active tablet cores. The desired tap and bulk densities of the granulation of the present invention are normally between from about 0.3 to about 0.8 g/ml, with an average density of from about 0.5 to about 0.7 g/ml.

The compression coatings of the present invention preferably have uniform packing characteristics over a range of different particle size distributions and are capable of processing onto the pre-formed tablet core using direct compression, following the addition of a lubricant.

In addition to being (optionally) used in the tablet core, in certain embodiments it is preferred that one or more pharmaceutically acceptable lubricants be added to the compression coating materials (preferably pre-agglomerated) prior to the mixture being compression coated onto the surface of the core. Examples of suitable lubricants for use in the core and compression coating of the invention include, for example and without limitation, talc, stearic acid, vegetable oil, calcium stearate, zinc stearate, magnesium stearate, etc. Preferably, an effective amount of any generally accepted pharmaceutical lubricant, including calcium or magnesium soaps is preferably added to the mixture of ingredients prior to compression of the mixture onto the solid pre-formed tablet core. An especially preferred lubricant is sodium stearyl fumarate, NF, commercially available under the trade name Pruv® from JRS Pharma LP.

In certain embodiments, the present invention is further directed towards a method of manufacturing the delayed release solid oral dosage forms (e.g., tablets) of the present invention. In certain preferred embodiments, the steps for preparation of a delayed release oral solid dosage form of the present invention may include the following:

Preparation of inner core formulation:
1. (A) Wet granulate active ingredient (e.g., drug) together with optional excipients, followed by drying and milling as necessary to obtain a granulate; or
    (B) Dry blend the active together with optional excipients using geometric dilution as necessary to obtain a granulate;
2. Optionally, extragranularly add excipients to the material prepared in Step 1 with appropriate blending;
3. Preferably, lubricate powder blend prepared in Step 1 or 2:
4. Compress core using powder blend prepared in Step 3 with an appropriate press.
5. Optionally, applying a functional film coating onto the tablet cores prepared in Step 4;

Preparation of delayed release (compression) coating may be accomplished, e.g., as follows:
6. (A) Wet granulate a gum(s) (e.g., a heteropolysaccharide gum and a homopolysaccharide gum) together with optional excipients to form a delayed release material (agglomerated particles), and then dry the delayed release material; or
    (B) Dry blend a gum(s) together with optional excipients to form a delayed release material (granulate);
7. Preferably, mill the delayed release material prepared in Step 6;
8. Preferably, lubricate the delayed release material prepared in Step 6 or 7;

Coating of inner core:
9. Compression coat the delayed release material prepared in Steps 6-8 over the tablet cores prepared in Step 1-5;
10. Optionally, film coat the final dosage form (if desired).

In certain embodiments, steps 4 & 10 are combined in a single unit operation when using e.g., a Dry-Cota Press as described hereinafter. A functional coating of the tablet cores may be possible using the Dry-Cota Press if a modification is made to the press to add a core tablet feeder system.

A Manesty Dry-Cota press consists of two side by side interconnected tablet presses where the core is made on one press then mechanically transferred to the next press for compression coating. Each "press" has an independent powder feed mechanism so that core blend is loaded on one machine and coating blend on the other. Mechanical transfer arms rotate between the machines to remove cores from one press and transfer them to the coating press. Other and more modem types of presses which may be used (e.g. Elizabeth Hata HT-AP44-MSU-C, Killian RUD, Fette PT 4090) have a dual feed system for coating blend and pre-made cores. This configuration is more flexible, in that cores can be pan coated with a functional or cosmetic coating before compression coating. In addition, this allows multiple compression coating layers to be achieved by recycling tablets that have already been compression coated. Both types of presses have mechanisms to center the tablet within the coating both vertically and radially. One of ordinary skill would understand that other tablet presses may be used to provide for the final dosage forms of the present invention.

Although typically the compression coating surrounds the entire core, in certain embodiments of the present invention, the compression coating substantially surrounds, but does not entirely surround the tablet core. In such instances, the release of drug from the tablet core will occur first from that portion of the inner core to which the compression coating is not applied. In other embodiments of the invention, compression coating is not applied to the same thickness around the entire inner core, thereby creating areas of the compressed dosage form that release drug earlier (and later) than other areas. This may be accomplished, e.g., by having the core to which the compression coating is applied not being centered in the press.

In certain embodiments the tablets formed from the compression coating of the core are from about 4 to about 25 kP, preferably about 5 to about 15 kP, most preferably about 8 to about 9 kP hardness. In certain preferred embodiments, for round compression coated tablets the diameter may be up to ⅝ inch or greater, and for caplet shaped compression coated tablets the diameter may be up to ¾ inch or greater. The average flow of the (non-compression) coatings prepared in accordance with the present invention is from about 25 to about 40 g/sec.

In certain embodiments of the present invention, the compression coated tablet may then be further overcoated with an enteric coating material or a hydrophobic material. Examples of suitable enteric polymers include cellulose acetate phthalate, hydroxypropyl-methylcellulose phthalate, polyvinylacetate phthalate, methacrylic acid copolymer, shellac, hydroxypropylmethylcellulose succinate, cellulose acetate trimellitate, and mixtures of any of the foregoing. An example of a suitable commercially available enteric material is available under the trade name Eudragit® L30D55.

In further embodiments, the dosage form may be coating with a hydrophilic coating in addition to or instead of the above-mentioned enteric coating or hydrophobic coating. An example of a suitable material that may be used for such a hydrophilic coating is hydroxypropylmethylcellulose (e.g., Opadry®, commercially available from Colorcon, West Point, Pa.).

In still further embodiments, the optional enteric and/or hydrophobic and/or hydrophilic coatings may be alternatively or additionally applied as an intermediate layer(s) between the core and the compression coating.

The optional enteric and/or hydrophobic and/or hydrophilic coatings may be applied in any pharmaceutically acceptable manner known to those skilled in the art. For example, in one embodiment, the coating is applied via a fluidized bed or in a coating pan. For example, the coated tablets may be dried, e.g., at about 60-70° C. for about 3-4 hours in a coating pan. The solvent for the hydrophobic polymer or enteric coating may be organic, aqueous, or a mixture of an organic and an aqueous solvent. The organic solvents may be, e.g., isopropyl alcohol, ethanol, and the like, with or without water.

In additional embodiments of the present invention, a support platform is applied to the tablets manufactured in accordance with the present invention. Suitable support platforms are well known to those skilled in the art. An example of suitable support platforms is set forth, e.g., in U.S. Pat. No. 4,839,177, hereby incorporated by reference. In that patent, the support platform partially coats the tablet, and consists of a polymeric material insoluble in aqueous liquids. The support platform may, for example, be designed to maintain its impermeability characteristics during the transfer of the therapeutically active medicament. The support platform may be applied to the tablets, e.g., via compression coating onto part of the tablet surface, by spray coating the polymeric materials comprising the support platform onto all or part of the tablet surface, or by immersing the tablets in a solution of the polymeric materials.

The support platform may have a thickness of, e.g., about 2 mm if applied by compression, and about 10μ if applied via spray-coating or immersion-coating. Generally, in embodiments of the invention wherein a hydrophobic polymer or enteric coating is applied to the tablets over the delayed release coating, the tablets are coated to a weight gain from about 1 to about 20%, and in certain embodiments preferably from about 5% to about 10%.

Materials useful in the hydrophobic coatings and support platforms of the present invention include derivatives of acrylic acid (such as esters of acrylic acid, methacrylic acid, and copolymers thereof) celluloses and derivatives thereof (such as ethylcellulose), polyvinylalcohols, and the like.

As mentioned above, the cores and/or compression coatings may also contain suitable quantities of, e.g., lubricants, binders, granulating aids, diluents, colorants, flavorants and glidants which are conventional in the pharmaceutical art.

Examples of suitable binders for use in the present invention include for example and without limitation, povidone, polyvinylpyrrolidone, xanthan gum, cellulose gums such as carboxymethylcellulose, methyl cellulose, hydroxypropylmethylcellulose, hydroxycellulose, gelatin, starch, and pregelatinized starch.

Examples of suitable glidants for use in the present invention include talc, silicon dioxide, and cornstarch.

In certain embodiments of the present invention, the tablet core includes an additional dose of the drug (or a therapeutically effective dose of a different drug) included in either the (optional) hydrophobic or enteric coating, or in an additional (optional) overcoating coated on the outer surface of the tablet core (without the hydrophobic or enteric coating) or as an additional coating layer coated on the surface of the base coating(s) comprising the compression coating and, if applicable, hydrophobic and/or enteric coating material. This may be desired when, for example, a loading dose of the drug is needed to provide therapeutically effective blood levels of the active agent when the formulation is first exposed to gastric fluid. The loading dose of drug included in the coating layer may be, e.g., from about 10% to about 40% of the total amount of drug included in the formulation.

Examples of drugs that are suitable for incorporation in the present invention include:
  antihistamines (e.g., azatadine maleate, brompheniramine maleate, carbinoxamine maleate, chlorpheniramine maleate, dexchlorpheniramine maleate, diphenhydramine hydrochloride, doxylamine succinate, methdilazine hydrochloride, promethazine, trimeprazine tartrate, tripelennamine citrate, tripelennamine hydrochloride and triprolidine hydrochloride);
  antibiotics (e.g., penicillin V potassium, cloxacillin sodium, dicloxacillin sodium, erythromycin, neomycin, nafcillin sodium, oxacillin sodium, carbenicillin indanyl sodium, oxytetracycline hydrochloride, tetracycline hydrochloride, clindamycin phosphate, clindamycin hydrochloride, clindamycin palmitate HCL, lincomycin HCL, novobiocin sodium, nitrofurantoin sodium, metronidazole hydrochloride); antituberculosis agents (e.g., isoniazid);
cholinergic agents (e.g., ambenonium chloride, bethanecol chloride, neostigmine bromide, pyridostigmine bromide);
antimuscarinics (e.g., anisotropine methylbromide, clidinium bromide, dicyclomine hydrochloride, glycopyrrolate, hexocyclium methylsulfate, homatropine methylbromide, hyoscyamine sulfate, methantheline bromide, hyoscine hydrobromide, oxyphenonium bromide, propantheline bromide, tridihexethyl chloride);
sympathomimetics (e.g., bitolterol mesylate, ephedrine, ephedrine hydrochloride, ephedrine sulphate, orciprenaline sulphate, phenylpropanolamine hydrochloride, pseudoephedrine hydrochloride, ritodrine hydrochloride, salbutamol sulphate, terbutaline sulphate);
sympatholytic agents (e.g., phenoxybenzamine hydrochloride); miscellaneous autonomic drugs (e.g., nicotine);
iron preparations (e.g., ferrous gluconate, ferrous sulphate);
haemostatics (e.g., aminocaproic acid);
cardiac drugs (e.g., acebutolol hydrochloride, disopyramide phosphate, flecainide acetate, procainamide hydrochloride, propranolol hydrochloride, quinidine gluconate, timolol maleate, tocainide hydrochloride, verapamil hydrochloride);
antihypertensive agents (e.g., captopril, clonidine hydrochloride, hydralazine hydrochloride, mecamylamine hydrochloride, metoprolol tartrate); vasodilators (e.g., papaverine hydrochloride);
non-steroidal anti-inflammatory agents (e.g., salicylates, choline salicylate, ibuprofen, indomethacin, ketoprofen, magnesium salicylate, meclofenamate sodium, naproxen sodium, tolmetin sodium);
opiate agonists (e.g., codeine hydrochloride, codeine phosphate, codeine sulphate, dextromoramide tartrate, hydrocodone bitartrate, hydromorphone hydrochloride, pethidine hydrochloride, methadone hydrochloride, morphine sulphate, morphine acetate, morphine lactate, morphine meconate, morphine nitrate, morphine monobasic phosphate, morphine tartrate, morphine valerate, morphine hydrobromide, morphine hydrochloride, propoxyphene hydrochloride);
anticonvulsants (e.g., phenobarbital sodium, phenytoin sodium, troxidone, ethosuximide, valproate sodium);
tranquilizers (e.g., acetophenazine maleate, chlorpromazine hydrochloride, fluphenazine hydrochloride, prochlorperazine edisylate, promethazine hydrochloride, thioridazine hydrochloride, trifluoperazine hydrochloride, lithium citrate, molindone hydrochloride, thiothixine hydrochloride);
chemotherapeutic agents (e.g., doxorubicin, cisplatin, floxuridine, methotrexate, combinations thereof, etc.);
lipid lowering agents (e.g., gemfibrozil, clofibrate, HMG-CoA reductase inhibitors, such as for example, atorvastatin, cerivastatin, fluvastatin, lovastatin, pravastatin, simvastatin, etc.);

H$_2$-antagonists (e.g., cimetidine, famotidine, nizatidine, ranitidine HCl, etc.);

anti-coagulant and anti-platelet agents (e.g., warfarin, cipyridamole, ticlopidine, etc.);

bronchodilators (e.g., albuterol, isoproterenol, metaproterenol, terbutaline, etc.);

stimulants (e.g., benzamphetamine hydrochloride, dextroamphetamine sulphate, dextroamphetamine phosphate, diethylpropion hydrochloride, fenfluramine hydrochloride, methamphetamine hydrochloride, methylphenidate hydrochloride, phendimetrazine tartrate, phenmetrazine hydrochloride, caffeine citrate);

barbiturates (e.g., amylobarbital sodium, butabarbital sodium, secobarbital sodium);

sedatives (e.g., hydroxyzine hydrochloride, methprylon); expectorants (e.g., potassium iodide);

antiemetics (e.g., benzaquinamide hydrochloride, metoclopropamide hydrochloride, trimethobenzamide hydrochloride);

gastro-intestinal drugs (e.g., ranitidine hydrochloride); heavy metal antagonists (e.g., penicillamine, penicillamine hydrochloride);

antithyroid agents (e.g., methimazole);

genitourinary smooth muscle relaxants (e.g., flavoxate hydrochloride, oxybutynin hydrochloride);

vitamins (e.g., thiamine hydrochloride, ascorbic acid);

unclassified agents (e.g., amantadine hydrochloride, colchicine, etidronate disodium, leucovorin calcium, methylene blue, potassium chloride, pralidoxime chloride, choroquine, iodochlorhydroxyquin, disodohydroxyquin.

steroids, particularly glucocorticoids (e.g., prednisolone, prednisolone phosphate, prednisolone metasulpho-benzoate sodium, prednisolone sodium phosphate, beclomethasone dipropionate, becloomethasone valerate, prednisone, cortisone, hydrocortisone, methylprednisolone, betamethasone, dexamethasone, triamcinolone).

compounds active in the relief of diarrhea compounds active in the relief of constipation compounds active in the relief of spasm and in the improvement of motility, e.g. peppermint oil and other carminative essential oils.

compounds for removal of excessive bile acids, e.g. cholestyramine.

Certain drugs which are particularly preferred are those for the treatment of chronic diseases of the bowel, particularly Crohn's disease and ulcerative colitis. These drugs may include certain antidiarrheal agents such as diphenoxylate, loperamide, codeine, and the like; antibiotics such as metronidazole, ampicillin, sulfonamide, cephalosporins, tetracycline, ciprofloxacin, and the like, immunomodulators such as azatiorprine and 6-mercapto-purine; aminosalicylates such as 5-amino salicylic acid (5-ASA), sulfasalazine, olsalazine, mesalamine, and balsalazide; immunosuppressive agents such as methotrexate and cyclosporine; and anti-tumor necrosis factor substances such as for example infliximab.

Particularly preferred are the glucocorticoids (also known as corticosteroids), particularly for treating irritable bowel diseases (IBD), ulcerative colitis or Crohn's disease. These include hydrocortisone, beclamethasone, betamethasone, cortisone, dexamethasone, flunisolide, methylprednisone, paramethasone, prednisolone, prednisone, triamcinolone, alclometasone, amcinonide, clobetasol, clocortilone, desonide, desoximetasone, diflorasone, fluocinolone, fluorometholone, flurandrenolide, halcinonide, medrysone, mometasone, budesonide, fluticasone, salts thereof and the like.

Other drugs that are particularly useful in the dosage forms of the present invention include stimulant laxatives (for example, docusate sodium, senna concentrates, bisacodyl, potassium bitartrate, and the like). The amount of the active drug that will be included in the composition will vary depending upon the activity of the drug relative to the condition being treated.

Any combinations of the aforementioned drugs may also be used.

The drugs may be in their base form, or a pharmaceutically acceptable salt or complex may be used. The list of possible therapeutic classes and particular drugs listed above are representative only, and are not meant to limit the scope of the invention in any way.

In certain embodiments, drugs for use in the present invention may also include polypeptides, proteins and derivatives thereof. Examples of such drugs include insulin, calcitonin, angiotensin, vasopressin, desmopressin, LH-RH (luteinizing hormone-releasing hormone), somatostatin, glucagon, oxytocin, gastrin, ciclosporin, somatomedin, secretin, h-ANP (human artial natriuretic peptide), ACTH (adrenocorticotropic hormone), MSH (melanocyte-stimulating hormone), beta-endorphin, muramyl dipeptide, enkephalin, neurotensin, bombesin, VIP (vasoacive intestinal polypeptide), CCK-8 (cholecystokinin-8), PTH (parathyroid hormone), CGRP (calcitonin gene-related peptide), TRH (thyrotropin-releasing hormone), endocerine, hGH (human growth hormone), cytokines (e.g., interleukin, interferon, colony-stimulating factor, and tumor necrosis factor), as well as derivatives thereof.

In certain embodiments, the drug for use in the present invention is a diagnostic agent, such as x-ray contrast agents (e.g., barium sulfate, Diatrizoate Sodium, other iodine containing contrast agents) ultrasound contrast agents (e.g., air-containing microspheres), contrast or enhancement agents for Magnetic Resonance Imaging, Tomography, or Positron Emission agents, and the like.

In certain embodiments the direct delivery of the drug to the colon enhances the amount of drug absorbed in the colon, and the amount of drug to which colon cells are directly exposed. In certain embodiments, the direct delivery or targeting of the drugs to the colon also decreases the systemic distribution of the drugs, thereby reducing undesirable and potentially harmful side effects. Further, the direct delivery of drugs to the colon may also decrease the required therapeutically effective dose. For example, in certain embodiments drugs such as steroids may be more efficiently absorbed in the large intestine than the rest of the gastrointestinal tract.

The formulations of the present invention may be utilized to treat any condition known (or which become known) to those skilled in the art which would benefit from such therapy. Targeting of drugs to the colon provides the ability to locally treat large bowel diseases, thus avoiding systemic effects of drugs or inconvenient and painful transcolonic administration of drugs. In certain embodiments, the colonic drug delivery system allows local and direct treatment of colonic disease, e.g., ulcerative colitis, Crohn's disease, or colon cancer, thus preferably reducing the dosage of the drugs and minimizing undesirable or harmful side effects.

In situations where the active agent is a low dose active agent (e.g., a drug administered in a (unit) dose amount from about 0.01 mg to about 40 mg), in certain preferred embodiments, the total tablet weight is from about 220 mg to about 900 mg; and the core weight is preferably from about 50 mg to about 170 mg. Preferably, the core is from about 5 to about 23 percent, most preferably about 18 to about 20 percent by weight of the total tablet weight. In embodiments wherein the active agent is a low dose active agent, the coating is preferably from about 150 mg to about 850 mg. Preferably, the coating is from about 75 to about 94 percent by weight, most preferably from about 78 to 80 percent by weight of the total tablet. Preferably, where the active dose is a low dose active agent, the ratio of the core to gum (in the compression coating) is from about 1:0.37 to about 1:5, preferably from about 1:0.37 to about 1:1.12, most preferably from about 1:0.75. Where the active dose is a low dose active agent, the ratio of the core to compression coating material (all ingredients) is preferably from about 1:2 to about 1:9, and in certain embodiments more preferably about 1:4.

In situations where the active agent is a relatively high dose active agent (e.g., a drug administered in a (unit) dose amount from about 41 mg to about 300 mg), the ratio of core to gum (in the compression coating) is from about 1:0.3 to about 1:3, preferably from about 1:0.6 to about 1:1.5. In certain embodiments, preferably where the active agent is a high dose active agent, the ratio of the core to compression coating material (all ingredients) is from about 1:1 to about 1:5, preferably from about 1:2 to about 1:3. In situations where the active agent is a relatively high dose active agent, the total tablet weight is preferably from about 500 mg to about 1500 mg, more preferably from about 750 mg to about 1000 mg.

In the appended examples, the cores comprising the active agent are typically compression coated with the coating formulation by hand on a rotary tablet press. In such a process, roughly half the outer core material is first added to the die. An inner core tablet is typically centered on the powder bed and is covered with the other half of the outer coating powder. However, one skilled in the art will appreciate that compression coating may be accomplished via automated tablet presses for commercialization. Prior to compression coating with any tablet press, preferably 0.75% Pruv® (sodium stearyl fumarate, NF) or another suitable lubricant is added to the compression coating material(s). In certain examples wherein the coatings are indicate by the gums, for example, 50% xanthan gum (XG), the coating comprises 50% xanthan gum diluted with dextrose; and for example 50% locust bean gum (LBG), the coating comprises 50% locust bean gum diluted with dextrose, etc.

DETAILED DESCRIPTION OF THE PREFERRED EMBODIMENTS

The following examples illustrate various aspects of the present invention. They are not to be construed to limit the claims in any manner whatsoever.

EXAMPLE 1

A delayed release material to be used in the compression coatings of the invention is prepared having the following formulation listed in Table 1:

TABLE 1

| Component | Percentage |
|---|---|
| 1. Xanthan Gum | 3 |
| 2. Locust Bean Gum | 4.5 |
| 3. Mannitol | 92.5 |
| 4. Water* | q.s. (20-40) |

*Removed during processing

The process for the preparation of the delayed release material is as follows:

Process:
1. The requisite amounts of xanthan gum, locust bean gum, and mannitol are dry blended in a high speed mixer/granulator for 3 minutes.
2. Water is added to the dry blended mixture, and granulated for another 3 minutes.
3. The granulation is then dried in a fluid bed dryer to a LOD (loss on drying) of less than about 10% by weight (e.g., 4-7% LOD).

EXAMPLE 2

A delayed release material to be used in the compression coating of the invention is prepared having the formulation listed in Table 2:

TABLE 2

| Component | Percentage |
|---|---|
| 1. Xanthan Gum | 6 |
| 2. Locust Bean Gum | 9 |
| 3. Mannitol | 85 |
| 4. Water* | q.s. (20-40) |

*Removed During Processing

Process:
The same process for Example 1 is used to prepare the delayed release material of Example 2 to be used in the compression coatings of the invention.

EXAMPLE 3

A delayed release material to be used in the compression coatings of the invention is prepared having the formulation listed in Table 3:

TABLE 3

| Component | Percentage |
|---|---|
| 1. Xanthan Gum | 20 |
| 2. Locust Bean Gum | 30 |
| 3. Mannitol | 50 |
| 4. Water* | q.s. (20-40) |

*Removed during processing

Process:
The same process for Example 1 is used to prepare the delayed release material of Example 3 to be used in the compression coatings of the invention.

EXAMPLE 4

A prednisone core composition was prepared having the ingredients set forth in Table 4:

TABLE 4

| Component | Percent | amt. (mg/tab) |
|---|---|---|
| 1. Prednisone, USP | 11.7 | 7.5 |
| 2. Prosolv*90 M | 67.0 | 42.9 |
| 3. Syloid** | 0.5 | 0.3 |
| 4. Talc | 3.8 | 2.4 |
| 5. Samarium Oxide*** | 9.4 | 6.0 |
| 6. Polyethylene Glycol 3350 | N/A | N/A |

TABLE 4-continued

| Component | Percent | amt. (mg/tab) |
|---|---|---|
| 7. Sodium Lauryl Sulfate | N/A | N/A |
| 8. Sodium Croscarmellose**** | 1.9 | 1.2 |
| 9. Explotab***** | 5.6 | 3.6 |
| 10. Sodium Stearyl Fumarate | 0.2 | 0.1 |
| Total weight | | 64.0 |

*Prosolv is a commercially available (from JRS Pharma) augmented microcrystalline cellulose.
**Syloid is a commercially available colloidal silicon dioxide.
***Samarium oxide is included in the cores in order to perform scintigraphic data analysis. It is understood that the formulations of the examples are meant to encompass cores that do not include samarium oxide.
****sodium croscarmellose is a disintegrant.
*****sodium starch glycolate is commercially available (from JRS Pharma) as Explotab.

The core composition of Example 4 was prepared using the following process.

Process:

1. Dispense (1), (2), (3) and (5) into V-Blender and blend for 10 minutes.
2. Dispense (8) and (9) into V-Blender and blend for 5 minutes.
3. Dispense (4) into V-Blender and blend for 5 minutes.
4. Dispense (6) and/or (7) into V-Blender (if applicable) and blend for 5 minutes
5. Dispense (10) into V-Blender and blend for 5 minutes.
6. Compress into tablets using 3/16" S.C. round beveled edge tooling.

EXAMPLE 5

A prednisone core composition including PEG (polyethylene glycol) was prepared having the ingredients set forth in Table 5:

TABLE 5

| Component | Percent | amt. (mg/tab) |
|---|---|---|
| 1. Prednisone, USP | 11.7 | 7.5 |
| 2. Prosolv 90 M | 38.9 | 24.9 |
| 3. Syloid | 0.5 | 0.3 |
| 4. Talc | 3.7 | 2.4 |
| 5. Samarium Oxide | 9.4 | 6.0 |
| 6. Polyethylene Glycol 3350 | 28.1 | 18.0 |
| 7. Sodium Lauryl Sulfate | N/A | N/A |
| 8. Sodium Croscarmellose | 1.9 | 1.2 |
| 9. Explotab | 5.6 | 3.6 |
| 10. Sodium Stearyl Fumarate | 0.2 | 0.1 |
| Total weight | | 64.0 |

Process:

The same process used to prepare the core composition of Example 4 was used to prepare the core composition of Example 5.

EXAMPLE 6

A prednisone core composition including SLS (sodium lauryl sulfate) and PEG (polyethylene glycol) was prepared having the ingredients set forth in Table 6:

TABLE 6

| Component | Percent | Amt. (mg/tab) |
|---|---|---|
| 1. Prednisone, USP | 11.7 | 7.5 |
| 2. Prosolv 90 M | 45.5 | 29.1 |
| 3. Syloid | 0.5 | 0.3 |
| 4. Talc | 3.7 | 2.4 |
| 5. Samarium Oxide | 9.4 | 6.0 |
| 6. Polyethylene Glycol 3350 | 18.7 | 12.0 |
| 7. Sodium Lauryl Sulfate | 2.8 | 1.8 |
| 8. Sodium Croscarmellose | 1.9 | 1.2 |
| 9. Explotab | 5.6 | 3.6 |
| 10. Sodium Stearyl Fumarate | 0.2 | 0.1 |
| Total weight | | 64.0 |

Process:

The same process used to prepare the core composition of Example 4 was used to prepare the core composition of Example 6.

EXAMPLES 7-9

In Examples 7-9, prednisone tablets were prepared having a core formulation of Example 5 and coatings as listed Table 7 below:

TABLE 7

| | Ex. 7 | | Ex. 8 | | Ex. 9 | |
|---|---|---|---|---|---|---|
| Component | % | mg/tab | % | mg/tab | % | mg/tab |
| 1. Core of Ex. 5 | 20.4 | 64.0 | 20.4 | 64.0 | 20.4 | 64.0 |
| 2. Delayed Release material of Ex. 1 | 79.0 | 248.0 | N/A | N/A | N/A | N/A |
| 3. Delayed Release material of Ex. 2 | N/A | N/A | 79.0 | 248.0 | N/A | N/A |
| 4. Delayed Release material of Ex. 3 | N/A | N/A | N/A | N/A | 79.0 | 248.0 |
| 5. Sodium Stearyl Fumarate | 0.6 | 2.0 | 0.6 | 2.0 | 0.6 | 2.0 |
| Tablet weight (mg) | | 314.0 | | 314.0 | | 314.0 |
| Hardness (Kp) | | 12.0 | | 12.0 | | 12.0 |

Process:

1. Dispense appropriate delayed release material from Example 1, 2 or 3, (numbers 2, 3, or 4 in above Table 7) and sodium stearyl fumarate (5) into V-Blender and blend for 5 minutes.
2. Set up tablet press with 5/16" S.C. round beveled edge tooling.
3. Dispense approximately 125 mg of the delayed release blend into the 5/16" die(lower layer) and smooth level the blend with a spatula.
4. Place the Inner core (1) in the center of the die on top of the bottom layer.
5. Dispense approximately 125 mg of the appropriate delayed release blend into the 5/16" die(upper layer) and smooth and level the blend with a spatula.
6. Compress the Lower Layer, Inner core and Upper Layer into a tablet.

The tablets of Examples 7-9 were tested using USP apparatus type III with 250 mL solution (pH 1.5) at 15 dips per minute (dpm) giving the following results listed in Table 8:

TABLE 8

| Time (hours) | Example 7 | Example 8 | Example 9 |
|---|---|---|---|
| 0.0 | 0.0 | 0.0 | 0.0 |
| 2.0 | 96.9 | 0.0 | 0.0 |
| 3.0 | 98.3 | 0.0 | 0.0 |
| 4.0 | 98.6 | 51.7 | 0.0 |
| 5.0 | 98.7 | 69.3 | 0.0 |
| 6.0 | 98.7 | 97.3 | 0.0 |
| 7.0 | 98.7 | 97.8 | 0.0 |
| 8.0 | 98.7 | 97.8 | 0.8 |
| 12.0 | 98.7 | 97.8 | 15.4 |

The formulation of Example 7 (% Gums of 7.5%) released significantly faster than the formulations of Example 8 (% Gums of 15.0%), and Example 9 (% Gums of 50.0%). As the amount of gum content is increased in the compression coating, there's a corresponding increase in lag time.

EXAMPLES 10-12

In Examples 10-12, prednisone tablets were prepared having a core formulation and coatings as listed Table 9 below:

TABLE 9

| Component | Ex. 10 % | Ex. 10 mg/tab | Ex. 11 % | Ex. 11 mg/tab | Ex. 12 % | Ex. 12 mg/tab |
|---|---|---|---|---|---|---|
| 1. Core of Ex. 4 | 20.4 | 64.0 | N/A | N/A | N/A | N/A |
| 2. Core of Ex. 5 | N/A | N/A | 20.4 | 64.0 | N/A | N/A |
| 3. Core of Ex. 6 | N/A | N/A | N/A | N/A | 20.4 | 64.0 |
| 4. Delayed Release material of Ex. 2 | 79.0 | 248.0 | 79.0 | 248.0 | 79.0 | 248.0 |
| 5. Sodium Stearyl Fumarate | 0.6 | 2.0 | 0.6 | 2.0 | 0.6 | 2.0 |
| Tablet weight (mg) | | 314.0 | | 314.0 | | 314.0 |
| Hardness (Kp) | | 8.0 | | 8.0 | | 8.0 |

Process:
1. Dispense delayed release material from Ex. 2 (4) and sodium stearyl fumarate (5) into V-Blender and blend for 5 minutes.
2. Set up tablet press with 5/16" S.C. round beveled edge tooling.
3. Dispense approximately 125 mg of the delayed release blend into the 5/16" die (lower layer) and smooth level the blend with a spatula.
4. Place the Inner core (1) or (2) or (3) in the center of the die on top of the bottom layer.
5. Dispense approximately 125 mg of the delayed release blend into the 5/16" die (upper layer) and smooth and level the blend with a spatula.
6. Compress the Lower Layer, Inner core and Upper Layer into a tablet.

The tablets of Examples 10-12 were tested using USP apparatus type III with 250 mL solution pH 1.5 at 15 dips per minute (dpm) giving the following results listed in Table 10:

TABLE 10

| Time (hours) | Example 10 | Example 11 | Example 12 |
|---|---|---|---|
| 0.0 | 0.0 | 0.0 | 0.0 |
| 3.0 | 0.0 | 0.0 | 0.0 |
| 4.0 | 15.4 | 35.8 | 27.8 |
| 5.0 | 66.4 | 81.8 | 73.6 |
| 6.0 | 93.8 | 96.8 | 104.1 |
| 7.0 | 102.8 | 97.1 | 104.1 |
| 8.0 | 103.0 | 97.1 | 104.1 |

Formulations of Example 11, and Example 12 with the surfactant(s) included in the core are slightly faster than the reference formulation of Example 10 without the surfactant in the core. The addition of surfactant slightly increases the dissolution profile.

EXAMPLE 13

Effect of Surfactants (Dispersing Agents) Polyethylene Glycol 3350 (PEG 3350)/Sodium Lauryl Sulfate (SLS) Bio-Analysis In Example 13, a biostudy was done using formulations prepared in accordance with the present invention. The study was a cross over design study consisting of five study periods of approximately 36 hours duration. Study periods 1-4 were separated by a minimum period of 72 hours between dosing and study period 5 was administered at least 14 days after the previous study period. Healthy male volunteers aged 18-65, with no history of adverse reaction to steroids, gastrointestinal diseases or gastrointestinal surgery other than appendicectomy were included in the biostudy. Scintigraphic images and blood samples were taken at intervals up to 24 hours after dosing to compare the transit and disintegration times of the formulation with the pharmacokinetic data. Ten subjects completed the study.

The Study Design was as Follows:
1. Number of Subjects: 10
2. The Dosing Regimen was as follows:
   Regimen A=Formulation of Example 10 (7.5 mg Prednisone) administered at approximately 9:00 am-2 hours after a standard breakfast.
   Regimen B=Formulation of Example 11 (7.5 mg Prednisone) administered at approximately 9:00 am-2 hours after a standard breakfast.
   Regimen C=Formulation of Example 12 (7.5 mg Prednisone) administered at approximately 9:00 am-2 hours after a standard breakfast.
   Regimen D=Immediate release 7.5 mg Prednisone tablets USP administered at approximately 9:00 am-2 hours after a standard breakfast.
   Regimen E=Formulation of Example 11 (7.5 mg Prednisone) administered at approximately 10:30 am-2 hours after a standard evening meal.
3. The Parameters Observed were as follows:
   a. Scintigraphic data analysis: To record movement of tablet from stomach to intestine. Scintigraphic data were analysed to obtain: gastric emptying time; small intestinal transit time; ileocaecal junction (ICJ) arrival time; residence time in ICJ; anatomical location and time of initial and complete disintegration of tablet core.
   b. Pharmacokinetics data analysis: Pharmacokinetic data were analysed to obtain $C_{max}$, $T_{max}$, $T_{lag}$, $AUC_{0-24}$, $AUC_{0-\infty}$, $\lambda z$, and $t\frac{1}{2}$.

The Scintigraphic Results were as Follows:
The time of complete disintegration for the Formulation of Example 10 was later than that for the Formulation of Example 11 and Example 12. The majority of tablets of the Formulation of Example 10 disintegrated in the colon and for the tablets of the Formulation of Examples 11 and 12 the majority of tablets disintegrated in the small bowel. Table 11 below lists the tablet disintegration (hours post-dose) for Regimens A, B, and C, and Table 12 below lists the location of the tablet disintegration of Regimens A, B, and C.

TABLE 11

Tablet disintegration (hours post-dose)

| Disintegration | Regimen A (Ex. 10, am) | Regimen B (CDS 11, am) | Regimen C (Ex. 12, am) |
|---|---|---|---|
| Initial | 4.91 ± 1.44 | 3.34 ± 0.89 | 3.10 ± 0.69 |
| Complete | 6.05 ± 3.31 | 3.71 ± 0.94 | 3.28 ± 0.71 |

TABLE 12

The location of tablet disintegration

Gastrointestinal tract region with number of subjects having release in the respective region

| | S | PSB | MSB | DSB | ICJ | AC | HF | TC | SF |
|---|---|---|---|---|---|---|---|---|---|
| Regimen A (Ex. 10, am) | | | | | | | | | |
| Initial disintegration | — | — | 1 | 2 | — | 1 | 4 | 2 | — |
| Complete disintegration | — | — | — | 3 | — | 1 | 2 | 3 | 1 |
| Regimen B (Ex. 11, am) | | | | | | | | | |
| Initial disintegration | — | — | 2 | 5 | 1 | 2 | — | — | — |
| Complete disintegration | — | — | — | 6 | — | 4 | — | — | — |
| Regimen C (Ex. 12, am) | | | | | | | | | |
| Initial disintegration | — | — | — | 6 | 2 | 1 | — | — | 1 |
| Complete disintegration | — | — | — | 5 | 2 | 2 | — | — | 1 |

S—stomach,
PSB—proximal small bowel,
MSB—mid small bowel,
DSB—distal small bowel,
ICJ—ileocaecal junction,
AC—ascending colon,
HF—hepatic flexure,
TC—transverse colon,
SF—splenic flexure The Pharmacokinetic results (mean values) of Regimens A, B, C, D, and E from the biostudy, are listed in Table 13 below:

TABLE 13

| Parameter | Regimen A (Ex. 10, am) | Regimen B (Ex. 11, am) | Regimen C (Ex. 12, am) | Regimen D (IR tablet, am) | Regimen E (Ex. 11, pm) |
|---|---|---|---|---|---|
| $C_{max}$ (ng/ml) | 48.82 ± 50.09 | 123.16 ± 64.38 | 109.14 ± 50.00 | 197.32 ± 30.95 | 174.53 ± 16.55 |
| $T_{max}$ (hours) | 6.00 | 4.50 | 4.75 | 1.00 | 3.50 |
| $T_{lag}$ (hours) | 3.75 | 3.00 | 3.50 | 0.50 | 3.00 |
| $AUC_{0-24}$ (ng · h/ml) | 293 ± 309 | 619 ± 367 | 563 ± 305 | 858 ± 148 | 883 ± 154 |
| $AUC_{0-\infty}$ (ng · h/ml) | 575 ± 327 | 959 ± 294 | 708 ± 392 | 1005 ± 39 | 923 ± 156 |
| $t_{1/2}$ (hours) | 3.37 ± 0.60 | 3.17 ± 0.14 | 3.40 ± 0.72 | 3.39± 0.01 | 3.58 ± 0.89 |

The delay in complete tablet disintegration for Regimen A compared with Regimens B and C is reflected in the slightly higher $T_{max}$ and the lower $C_{max}$ values for Regimen A than for Regimens B and C. The $AUC_{0-24}$ values of prednisolone were lower for Regimen A compared with Regimens B and C. Compared with the IR tablets the $C_{max}$ and $AUC_{0-24}$ values of prednisolone were approximately 33% lower for Regimen B and 39% lower for Regimen C. The $C_{max}$ and $AUC_{0-24}$ values for the formulation of Example 11 administered in the evening were approximately 1.4-fold higher than those values for the formulation of Example 11 administered in the morning.

The addition of a dispersing agent (e.g., a surfactant) resulted in significant increases in $C_{max}$ and AUC.

Night time dosing resulted in higher $C_{max}$ and AUC values with less variability. These values compare better to the IR product than Regimen A, B, C.

Conclusion:

For the delayed release delivery systems administered in the morning, the time of complete disintegration was later for the formulation of Example 10 than for the formulations of Examples 11 and 12. Disintegration of the formulations of Examples 11 and 12 occurred higher in the gastrointestinal tract than the formulation of Example 10. In the majority of subjects disintegration of the formulation of Example 10 occurred in the colon and disintegration of the formulations of Example 11 and 12 occurred in the small intestine. The pharmacokinetic parameters for the three systems reflect these differences in disintegration with the rate and extent of absorption for prednisolone higher for the formulations of Example 11 and 12 than for Example 10, and $T_{max}$ and $T_{lag}$ occurring later for Example 10 than for Examples 11 and 12. Compared with the immediate release tablet formulation the rate and extent of absorption were lower for the delayed release delivery systems. Administration of Example 11 in the evening resulted in a higher rate and extent of absorption of prednisolone than administration of Example 11 in the morning.

EXAMPLE 14

A budesonide core composition was prepared having the ingredients set forth in Table 14. Budesonide is an anti-inflammatory steroid drug that has been used in the management of colonic diseases such as micro-ulcerative colitis, Chron's disease, etc.

TABLE 14

| Component | Percent | amt. (mg/tab) |
|---|---|---|
| 1. Budesonide | 14.06 | 9.0 |
| 2. Prosolv 90 | 78.28 | 50.1 |
| 3. Explotab | 5.62 | 3.6 |
| 4. Na CMC | 1.88 | 1.2 |

TABLE 14-continued

| Component | Percent | amt. (mg/tab) |
|---|---|---|
| 5. Pruv* | 0.16 | 0.1 |
| TOTAL | 100.00 | 64.0 |

*sodium stearyl fumarate, commercially available as Pruv from JRS Pharma LP.

Process:
1. Screen Materials through 30 mesh screen
2. Add components 1,2 into V-Blender and mix for 10 minutes
3. Add components 3 and 4 into V-Blender and mix for 5 minutes
4. Add components 5 into V-Blender and mix for 5 minutes
5. Compress into 9 mg tablets using 3/16" round beveled concave (0.1875" Dia.) tooling.

EXAMPLES 15-17

In examples 15-17 budesonide tablets were prepared having a core composition of Example 14 and coatings listed as in Table 15 below.

TABLE 15

| Component | Ex. 15 (7.5% gum coating) | | Ex. 16 (15% gum coating) | | Ex. 17 (50% gum coating) | |
|---|---|---|---|---|---|---|
| | % | mg/tablet | % | mg/tablet | % | mg/tablet |
| 1. Core of Ex. 14 | 20 | 64 | 20 | 64 | 20 | 64 |
| 2. Delayed Release Material of Ex. 1 | 80 | 250 | | | | |
| 3. Delayed Release Material of Ex. 2 | | | 80 | 250 | | |
| 4. Delayed Release Material of Ex. 3 | | | | | 80 | 250 |
| Tablet Weight (mg) | | 314 | | 314 | | 314 |
| Hardness (Kp) | | 10-12 | | 10-12 | | 7-12 |

Process:
1. Dispense appropriate release material from Example 1, 2, or 3 (numbers 2, 3, 4 in above Table 15).
2. Set up tablet press with 5/16" round beveled concave (0.3125" Dia.) tooling.
3. Dispense approximately 125 mg of the delayed release blend into the die (lower layer) and smooth and level the blend with a spatula.
4. Place the inner core (Ex. 14) in the center of the die top of the bottom layer.
5. Advance the press to lower the bottom layer into the die hole with the inner core in the center.
6. Dispense approximately 125 mg of the appropriate delayed release blend into the die (upper layer) and smooth and level the blend with a spatula.
7. Compress the Lower Layer, Inner Core and Upper Layer into a tablet.

The tablets from Examples 15 (7.5% gum coating) and 16 (15% gum coating) were tested using USP apparatus Type III changing the pH from 1.5 to 5.5 to 7.5 every two hours to simulate the travel of the tablet through the GI tract. Example 17 (50% gum coating) was also tested using USP apparatus Type III, but was kept at pH 5.5 for 4 rather than 2 hours because of its longer release time due to the higher gum ratio. Tests were performed with 250 mL solution at 15 dips per minute (dpm) and gave the following results listed in Table 16.

The percent of Budesonide released from different formulations as a function of time is listed in Table 16 below:

TABLE 16

| Time (hours) | Example 15 (7.5% gum coating) | Example 16 (15% gum coating) | Example 17 (50% gum coating) |
|---|---|---|---|
| 0.0 | 0.0 | 0.0 | 0.0 |
| 1.0 | 91.2 | | |
| 2.0 | 92.9 | 0.0 | 0.0 |
| 4.0 | 93.6 | 0.0 | |
| 6.0 | 93.9 | 0.0 | 0.0 |
| 8.0 | 94.1 | 45.3 | |
| 10.0 | | 82.2 | |
| 12.0 | | 95.8 | |
| 14.0 | | | 13.0 |
| 18.0 | | | 55.6 |
| 22.0 | | | 89.4 |
| 26.0 | | | 92.4 |

The tablets from Examples 15 (7.5% gum coating) 16 (15% gum coating) and 17 (50% gum coating) were also tested using USP apparatus Type III maintaining the pH at 1.5 with sampling times the same as the previous tested dosage forms to ensure compatibility with previous testing. Tests were performed in 250 mL solution at 15 dips per minute (dpm) and gave the following results listed in Table 17.

The percent of Budesonide released from different formulations at pH 1.5 as a function of time is listed in Table 17 below:

TABLE 17

| Time (hours) | Example 15 (7.5% gum coating) | Example 16 (15% gum coating) | Example 17 (50% gum coating) |
|---|---|---|---|
| 0.0 | 0.0 | 0.0 | 0.0 |
| 1.0 | 47.6 | | |
| 2.0 | 99.6 | 0.0 | 0.0 |
| 4.0 | 101.4 | 91.4 | |
| 6.0 | 101.8 | 93.9 | 0.0 |
| 8.0 | 102.1 | 94.2 | |
| 10.0 | | 94.4 | |
| 12.0 | | 94.5 | |
| 14.0 | | | 3.5 |
| 18.0 | | | 75.7 |
| 22.0 | | | 87.6 |
| 26.0 | | | 92.8 |

In both release media, the formulation of Example 15 (7.5% gum coating) released significantly faster than the formulations of example 16 (15% gum coating) and Example 17 (50% gum coating). As the amount of gum in the compression coating is increased, there is a corresponding increase in lag time. This effect can be used to tailor the lag time to allow drug release to occur mainly in the colon.

The examples provided above are not meant to be exclusive. Many other variations of the present invention would be obvious to those skilled in the art, and are contemplated to be within the scope of the appended claims.

What is claimed is:
1. A delayed release oral solid dosage form comprising:
i) an immediate release core comprising a therapeutically effective amount of a drug which can be absorbed in the colon; from about 5% to about 50% of at least two surfactants by weight of the core, wherein one of the surfactants is polyethylene glycol; and ii) a delayed release material compression coated onto the surface of said core, said delayed release material consisting of a mixture of a heteropolysaccharide gum and a homopolysaccharide gum and iii) a material selected from the group consisting of a monosaccharide selected from the group consisting of dextrose and fructose, a disaccharide selected from the group consisting of sucrose and lactose, a polyhydric alcohol selected from the group consisting of xylitol, sorbitol, and mannitol, microcrystalline cellulose, starches, and any combinations or mixtures thereof; said mixture being compression coated in an amount effective to impart a desired delayed release such that said dosage form provides no release of drug until at least about 2 hours after oral administration of the dosage form, and the inclusion of the surfactant in the core facilitates the release of the drug from the dosage form in less than about 4 hours after initial release; said dosage form providing an in-vitro dissolution rate of the dosage form, when measured by the USP apparatus type III with 250 mL solution (pH 1.5) at 15 dpm that is 0% by weight drug released at about 3 hours, from about 5% to about 40% by weight drug release at about 4 hours, from about 30% to about 90% by weight drug released at 5 hours and greater than about 60% by weight drug released after 6 hours.

2. The delayed release oral solid dosage form of claim 1, wherein said core is a compressed core.

3. The delayed release oral solid dosage form of claim 1 wherein said core further comprises a disintegrant.

4. The delayed release oral solid dosage form of claim 3, wherein said core comprises from about 5 to about 20 percent disintegrant, by weight.

5. The delayed release oral solid dosage form of claim 3, wherein said disintegrant is selected from the group consisting of starch, veegum, crospovidone, cellulose, kaolin, microcrystalline cellulose, crosslinked polyvinyl pyrrolidone, croscarmellose sodium, crospovidone, crosslinked carboxy methyl cellulose, sodium starch glycolate, and mixtures thereof.

6. The delayed release oral solid dosage form of claim 1, wherein said heteropolysaccharide gum and said homopolysaccharide gum are agglomerated with said second excipient prior to being compression coated onto said core.

7. The delayed release oral solid dosage form of claim 6, wherein said second excipient is a monosaccharide selected from the group consisting of dextrose and fructose, a disaccharide selected from the group consisting of sucrose, and lactose, a polyhydric alcohol selected form the group consisting of xylitol, sorbitol and mannitol, microcrystalline cellulose, starches and any combinations or mixtures thereof.

8. The delayed release oral dosage form of claim 1, wherein the delayed release material comprises from about 7.5 to about 50 percent gum from (i), and from about 30 to about 95 percent material from (iii).

9. The delayed release oral solid dosage form of claim 8, wherein said gums comprise a mixture of xanthan gum and locust bean gum.

10. The delayed release oral solid dosage form of claim 9, wherein the xanthan gum and locust bean gum are in a ratio of about 1:3 to about 3:1.

11. The delayed release oral solid dosage form of claim 1, wherein the drug is selected from the group consisting of an antidiarrheal, an antibiotic, an immunomodulators, an aminosalicylates, an immunosuppressive agent, an anti-tumor necrosis factor substance, a glucorticoid, polypeptides, and proteins, and combinations thereof.

12. The delayed release oral solid dosage form of claim 1, wherein the drug is delivered to provide a local therapeutic effect.

13. The delayed release oral solid dosage form of claim 1, wherein the drug is delivered to provide a systemic therapeutic effect.

14. The delayed release oral solid dosage form of claim 1, wherein the drug is delivered to provide a local and systemic therapeutic effect.

15. The delayed release oral solid dosage form of claim 1, wherein said dosage form provides an in vitro dissolution rate, when measured by the USP apparatus Type III, with 250 ml solution pH 1.5 at 15 dpm that is 0% by weight drug released at about 3 hours, from about 10% to about 40% by weight drug release at about 4 hours, from about 60% to about 90% by weight drug released at 5 hours and greater than about 85% by weight drug released after 6 hours.

16. The delayed release dosage form of claim 1, wherein said dosage form does not have an intermediate coating between the compression coating and the core.

17. The delayed release oral solid dosage form of claim 1, wherein said gums comprise a mixture of xanthan gum and locust bean gum.

* * * * *